United States Patent
Taki

(10) Patent No.: US 11,497,458 B2
(45) Date of Patent: Nov. 15, 2022

(54) RADIOGRAPHIC IMAGE PROCESSING DEVICE, RADIOGRAPHIC IMAGE PROCESSING METHOD, AND RADIOGRAPHIC IMAGE PROCESSING PROGRAM

(71) Applicant: FUJIFILM Corporation, Tokyo (JP)

(72) Inventor: Tomoko Taki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 25 days.

(21) Appl. No.: 17/322,704

(22) Filed: May 17, 2021

(65) Prior Publication Data

US 2021/0393227 A1    Dec. 23, 2021

(30) Foreign Application Priority Data

Jun. 23, 2020   (JP) .............................. JP2020-108002

(51) Int. Cl.
  *A61B 6/00*      (2006.01)
(52) U.S. Cl.
  CPC .............. *A61B 6/505* (2013.01); *A61B 6/463* (2013.01); *A61B 6/466* (2013.01); *A61B 6/482* (2013.01)
(58) Field of Classification Search
  CPC ......... A61B 6/505; A61B 6/463; A61B 6/466; A61B 6/482; A61B 6/5217
  See application file for complete search history.

(56) References Cited

U.S. PATENT DOCUMENTS

| | | | |
|---|---|---|---|
| 5,931,780 A | 8/1999 | Giger et al. | |
| 2011/0305405 A1 | 12/2011 | Kawamura | |
| 2016/0140720 A1 | 5/2016 | Naito | |
| 2018/0028139 A1 | 2/2018 | Kuwabara | |
| 2019/0362492 A1* | 11/2019 | Kawamura | ........... G06T 7/0016 |
| 2019/0374184 A1* | 12/2019 | Takahashi | ............ A61B 6/4291 |
| 2019/0374185 A1* | 12/2019 | Takahashi | .............. A61B 6/463 |

FOREIGN PATENT DOCUMENTS

| | | |
|---|---|---|
| JP | H09-508813 A | 9/1997 |
| JP | 2011-255060 A | 12/2011 |
| JP | 2015-043959 A | 3/2015 |
| JP | 2018-015453 A | 2/2018 |
| JP | 2019-202035 A | 11/2019 |

* cited by examiner

*Primary Examiner* — Courtney D Thomas
(74) *Attorney, Agent, or Firm* — Studebaker & Brackett PC

(57) ABSTRACT

A processor acquires first-direction and second-direction radiographic images captured by emitting radiation in different directions. The processor derives a bone mineral content for each pixel in the bone portion included in the first-direction and second-direction radiographic images. The processor divides the bone portion included in the first-direction and second-direction radiographic images into a plurality of small regions and derives first and second evaluation results for each small region of the bone portion on the basis of the derived bone mineral content.

15 Claims, 15 Drawing Sheets

FIG. 20
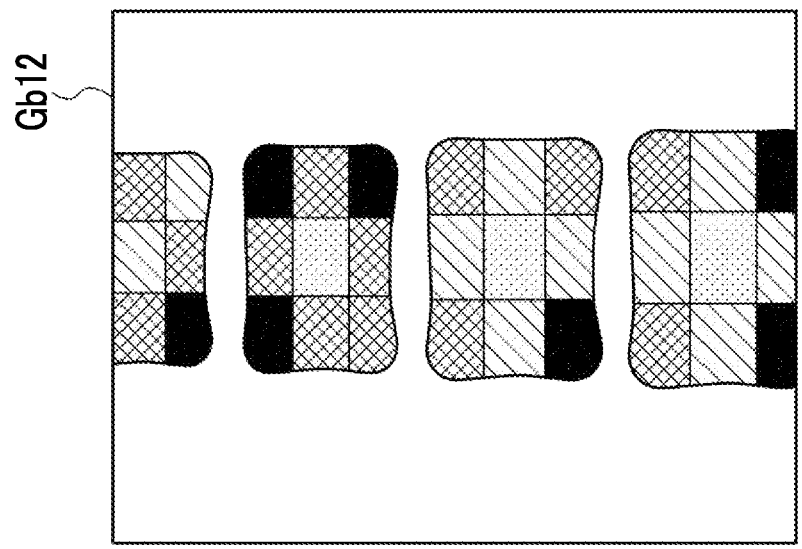
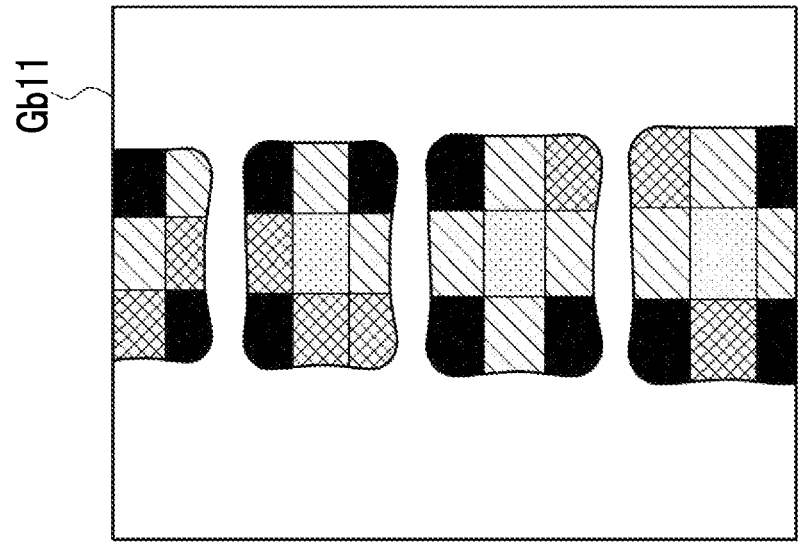

RADIOGRAPHIC IMAGE PROCESSING DEVICE, RADIOGRAPHIC IMAGE PROCESSING METHOD, AND RADIOGRAPHIC IMAGE PROCESSING PROGRAM

CROSS REFERENCE TO RELATED APPLICATIONS

The present application claims priority under 35 U.S.C. § 119 to Japanese Patent Application No. 2020-108002 filed on Jun. 23, 2020. The above application is hereby expressly incorporated by reference, in its entirety, into the present application.

BACKGROUND

Technical Field

The present disclosure relates to a radiographic image processing device, a radiographic image processing method, and a radiographic image processing program.

Related Art

A dual X-ray absorptiometry (DXA) method is known as one of the typical bone mineral quantification methods that are used to diagnose bone density in a bone-related disease such as osteoporosis. The DXA method calculates a bone mineral content from the pixel values of a radiographic image obtained by imaging with radiation having two types of energy, using the fact that the radiation which is incident on and transmitted through the human body is subjected to attenuation characterized by a mass attenuation coefficient $\mu$ ($cm^2/g$) that depends on a material (for example, bones) forming the human body, the density $\rho$ ($g/cm^3$) of the material, and the thickness t (cm) of the material.

In addition, a radiography apparatus is known which comprises two radiation detectors that include a plurality of pixels accumulating charge corresponding to the emitted radiation. The two radiation detectors are disposed so as to be stacked. Further, a technique is known which measures the bone mineral content of a subject using each electric signal corresponding to the dose of radiation emitted to each radiation detector in this type of radiography apparatus (see JP2018-015453A). Furthermore, there is a technique that measures the bone mineral content using a computed tomography (CT) image.

In addition, a method has been proposed which analyzes the bone mass and bone structure of a bone region on the basis of a radiographic image to derive the risk of future fractures (see JP1997-508813A (JP-H09-508813A)). Further, there is a method that measures a bone mineral content for each partial region of a bone region (see JP2019-202035A). The method disclosed in JP2019-202035A divides a vertebra into a cancellous bone region and a cortical bone region or divides the femur into a femoral neck region and other regions and measures the bone mineral content in the divided partial region.

However, the bone has a three-dimensional shape. Therefore, it is difficult to understand the three-dimensional state of the bone portion even in a case in which the partial region of the bone portion on the two-dimensional image is used as in the method disclosed in JP2019-202035A.

SUMMARY OF THE INVENTION

The present disclosure has been made in view of the above-mentioned problems, and an object of the present disclosure is to provide a technique that enables a user to understand the three-dimensional state of a bone portion.

According to an aspect of the present disclosure, there is provided a radiographic image processing device comprising at least one processor. The processor is configured to: acquire at least one first-direction radiographic image on the basis of first imaging that irradiates a subject including a bone portion with radiation in a first direction and acquire at least one second-direction radiographic image on the basis of second imaging that irradiates the subject with the radiation in a second direction different from the first direction; derive a bone mineral content for each pixel in the bone portion included in each of the first-direction radiographic image and the second-direction radiographic image; and divide the bone portion included in the first-direction radiographic image into a plurality of small regions, derive a first evaluation result for the bone portion in each small region on the basis of the bone mineral content derived for the first-direction radiographic image, divide the bone portion included in the second-direction radiographic image into a plurality of small regions, and derive a second evaluation result for the bone portion in each small region on the basis of the bone mineral content derived for the second-direction radiographic image.

In addition, an angle formed between the first direction and the second direction is preferably equal to or greater than 60 degrees and equal to or less than 120 degrees, more preferably equal to or greater than 80 degrees and equal to or less than 100 degrees, and most preferably 90 degrees. That is, in the radiographic image processing device according to the aspect of the present disclosure, the first direction may be a direction in which a front or back of the subject is irradiated with the radiation, and the second direction may be a direction in which a side of the subject is irradiated with the radiation. In this case, the angle formed between the first direction and the second direction is 90 degrees.

Further, in the radiographic image processing device according to the aspect of the present disclosure, the processor may be configured to: derive a maximum value of a first body thickness of the subject in the first direction on the basis of the second-direction radiographic image and derive a maximum value of a second body thickness of the subject in the second direction on the basis of the first-direction radiographic image; and derive the bone mineral content, from which an influence of a scattered ray component of the radiation included in the first-direction radiographic image and the second-direction radiographic image has been removed, on the basis of the maximum value of the first body thickness and the maximum value of the second body thickness.

In this case, the processor may be configured to derive the bone mineral content, from which the influence of the scattered ray component of the radiation has been removed, on the basis of radiation characteristics of an object interposed between a radiation source that emits the radiation and radiation detectors that acquire the first-direction radiographic image and the second-direction radiographic image.

Further, in the radiographic image processing device according to the aspect of the present disclosure, the processor may be configured to: perform, as the first imaging, imaging that irradiates the subject with radiation having different energy distributions in the first direction to acquire a first radiographic image and a second radiographic image as the first-direction radiographic images; derive a first bone portion image, in which the bone portion of the subject has been highlighted, on the basis of the first radiographic image and the second radiographic image; and derive the bone mineral content for each pixel of the first-direction radiographic image on the basis of the first bone portion image.

Furthermore, in the radiographic image processing device according to the aspect of the present disclosure, the processor may be configured to: perform, as the second imaging, imaging that irradiates the subject with radiation having different energy distributions in the second direction to acquire a third radiographic image and a fourth radiographic image as the second-direction radiographic images; derive a second bone portion image, in which the bone portion of the subject has been highlighted, on the basis of the third radiographic image and the fourth radiographic image; and derive the bone mineral content for each pixel of the second-direction radiographic image on the basis of the second bone portion image.

Moreover, in the radiographic image processing device according to the aspect of the present disclosure, in a case in which the bone portion is a vertebral body included in a vertebra, the small regions may be regions obtained by dividing the vertebral body in at least one of an up-down direction or a left-right direction in the first-direction radiographic image and the second-direction radiographic image.

In addition, in the radiographic image processing device according to the aspect of the present disclosure, the processor may be configured to derive the first evaluation result and the second evaluation result on the basis of an alignment of a spine in a case in which the bone portion is a vertebral body included in a vertebra.

Further, in the radiographic image processing device according to the aspect of the present disclosure, the processor may be configured to derive the first evaluation result and the second evaluation result only for a cancellous bone region in a case in which the bone portion is a vertebral body included in a vertebra.

Further, in the radiographic image processing device according to the aspect of the present disclosure, the processor may be configured to display the first evaluation result and the second evaluation result on a display.

Further, in the radiographic image processing device according to the aspect of the present disclosure, the processor may be configured to display the first evaluation result and the second evaluation result so as to be superimposed on a three-dimensional image of the bone portion.

Further, in the radiographic image processing device according to the aspect of the present disclosure, the processor may be configured to: acquire a plurality of first-direction radiographic images and a plurality of second-direction radiographic images captured at different imaging times; derive the bone mineral content for each imaging time; and derive the first evaluation result and the second evaluation result on the basis of a change in the bone mineral content of each of the small regions of the plurality of first-direction radiographic images and the plurality of second-direction radiographic images over time.

Further, in the radiographic image processing device according to the aspect of the present disclosure, the first evaluation result and the second evaluation result may be an effectiveness of a medicine on the bone portion.

According to another aspect of the present disclosure, there is provided a radiographic image processing method comprising: acquiring at least one first-direction radiographic image on the basis of first imaging that irradiates a subject including a bone portion with radiation in a first direction and acquiring at least one second-direction radiographic image on the basis of second imaging that irradiates the subject with the radiation in a second direction different from the first direction; deriving a bone mineral content for each pixel in the bone portion included in each of the first-direction radiographic image and the second-direction radiographic image; and dividing the bone portion included in the first-direction radiographic image into a plurality of small regions, deriving a first evaluation result for the bone portion in each small region on the basis of the bone mineral content derived for the first-direction radiographic image, dividing the bone portion included in the second-direction radiographic image into a plurality of small regions, and deriving a second evaluation result for the bone portion in each small region on the basis of the bone mineral content derived for the second-direction radiographic image.

In addition, a program that causes a computer to perform the radiographic image processing method according to the aspect of the present disclosure may be provided.

According to the present disclosure, it is possible to understand the three-dimensional state of a bone portion.

BRIEF DESCRIPTION OF THE DRAWINGS

FIG. 20 is a diagram illustrating the comparison of the bone mineral content over time.

DETAILED DESCRIPTION

Figure 1:
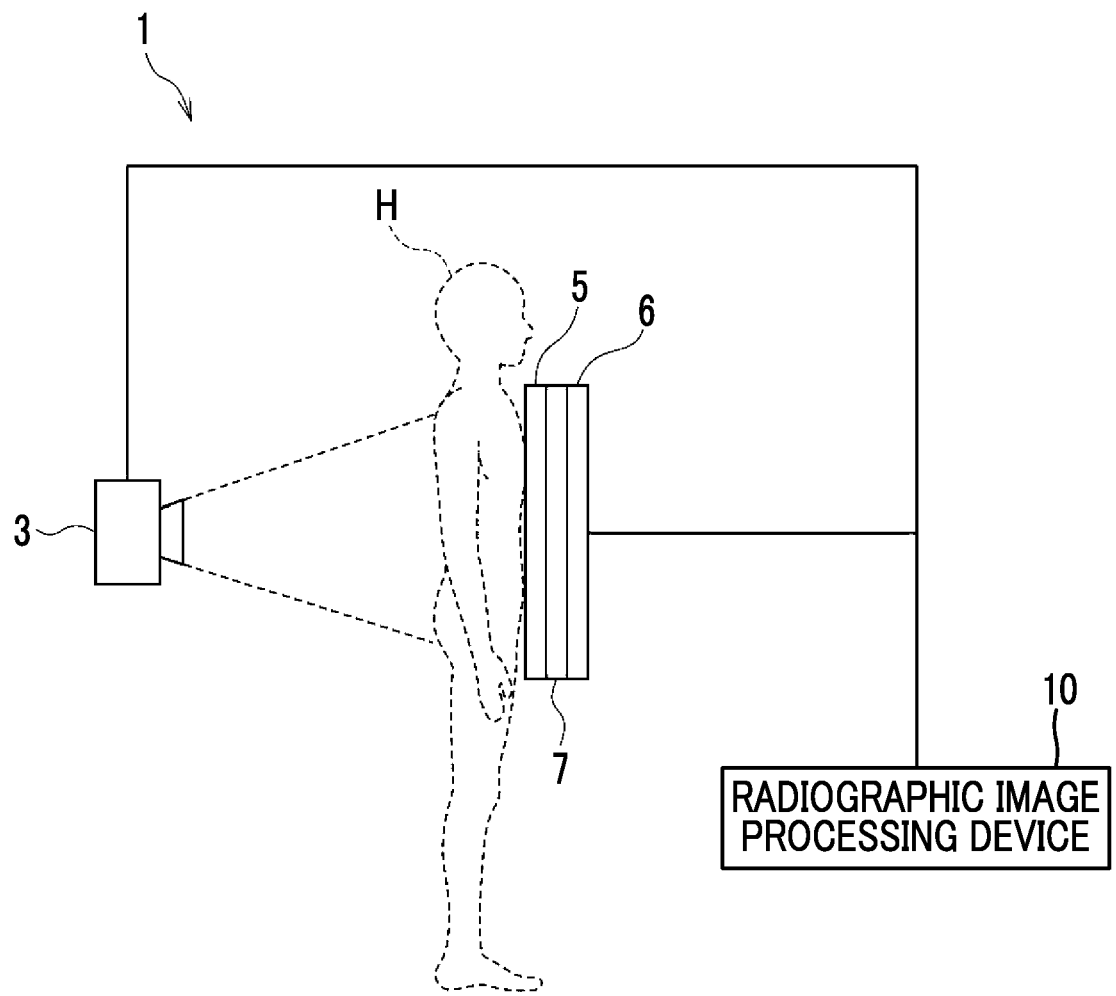
FIG. 1 is a block diagram schematically illustrating a configuration of a radiography system to which a radiographic image processing device according to an embodiment of the present disclosure is applied.

Hereinafter, embodiments of the present disclosure will be described with reference to the drawings. FIG. 1 is a block diagram schematically illustrating a configuration of a radiography system to which a radiographic image processing device according to an embodiment of the present disclosure is applied. As illustrated in FIG. 1, the radiography system according to this embodiment comprises an imaging apparatus 1 and a radiographic image processing device 10 according to this embodiment.

The imaging apparatus 1 performs so-called one-shot energy subtraction that irradiates a first radiation detector 5 and a second radiation detector 6 with X-rays which have been emitted from an X-ray source 3 and transmitted through a subject H while changing energy. At the time of imaging, as illustrated in FIG. 1, the first radiation detector 5, an X-ray energy conversion filter 7, and the second radiation detector 6 are disposed in this order from the side closer to the X-ray source 3, and the X-ray source 3 is driven. The X-ray energy conversion filter 7 is configured by a metal plate, such as a copper plate, that can absorb a specific energy component included in the X-rays.

Each of the first and second radiation detectors 5 and 6 generates a radiographic image on the basis of the X-rays which have been emitted from the X-ray source 3 and transmitted through the subject H. The first and second radiation detectors 5 and 6 may have the form of a so-called flat panel detector (FPD) in which thin film transistor (TFT) switches are turned on and off to read radiographic image signals. In this case, the first and second radiation detectors 5 and 6 may be a direct type that is directly irradiated with radiation and generates charge or an indirect type that converts radiation into visible light and then converts the visible light into a charge signal. In addition, a computed radiography (CR) technique that emits laser beams to read an image recorded on an imaging plate may be applied to the first and second radiation detectors 5 and 6.

One-shot energy subtraction is achieved by capturing the image of the subject H in a state in which the first radiation detector 5, the X-ray energy conversion filter 7, and the second radiation detector 6 are stacked in the order illustrated in FIG. 1. That is, two radiographic images having different energy distributions are acquired from the first radiation detector 5 and the second radiation detector 6.

The first radiation detector 5 acquires the radiographic image of the subject H obtained by low-energy X-rays including so-called soft rays. Further, the second radiation detector 6 acquires the radiographic image of the subject H obtained by high-energy X-rays excluding soft rays. The acquired radiographic images are input to the radiographic image processing device 10.

Here, in this embodiment, first, as illustrated in FIG. 1, first imaging is performed in which the chest of the subject H faces the first radiation detector 5 and the second radiation detector 6 and the subject H is irradiated with X-rays from the back of the subject H. Therefore, the first radiation detector 5 acquires a first radiographic image G1 which is a front image of the chest and abdomen of the subject H obtained by low-energy X-rays. The second radiation detector 6 acquires a second radiographic image G2 which is a front image of the chest and abdomen of the subject H obtained by high-energy X-rays. The first radiographic image G1 and the second radiographic image G2 correspond to first-direction radiographic images according to the present disclosure.

In addition, in this embodiment, in a case in which the image of the subject H is captured, a scattered ray removal grid that removes a scattered ray component of the X-rays transmitted through the subject H is not used. Therefore, the first radiographic image G1 and the second radiographic image G2 include a primary ray component and a scattered ray component of the X-rays transmitted through the subject H.

Figure 2:
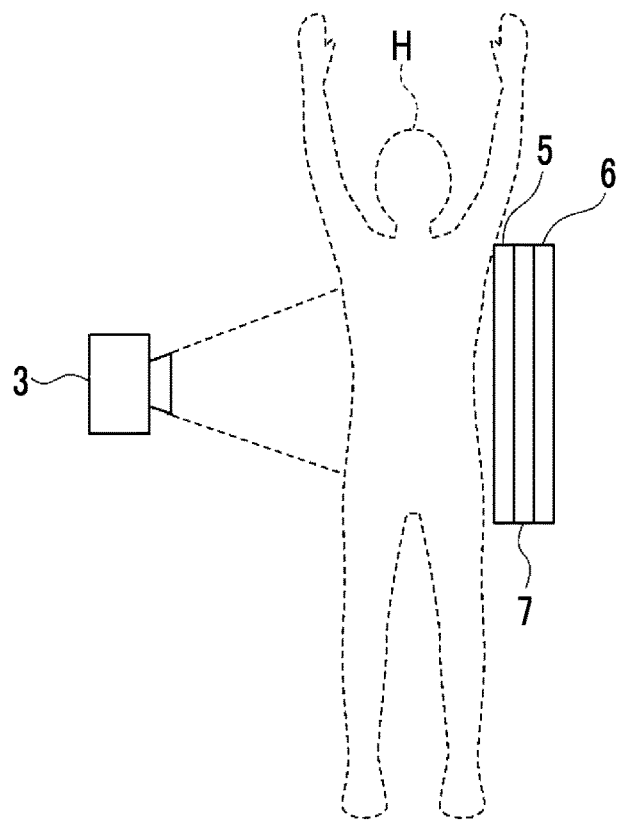
FIG. 2 is a block diagram schematically illustrating the capture of an image of a subject from the side in the radiography system to which the radiographic image processing device according to the embodiment of the present disclosure is applied.

Further, in this embodiment, as illustrated in FIG. 2, second imaging is performed in which the side of the subject H faces the first radiation detector 5 and the second radiation detector 6 and the subject H is irradiated with X-rays from the side of the subject H. Therefore, the first radiation detector 5 acquires a third radiographic image G3 which is a side image of the chest and abdomen of the subject H obtained by low-energy X-rays. The second radiation detector 6 acquires a fourth radiographic image G4 which is a side image of the chest and abdomen of the subject H obtained by high-energy X-rays. The third radiographic image G3 and the fourth radiographic image G4 correspond to second-direction radiographic images according to the present disclosure.

The radiographic image processing device 10 has a function of deriving an evaluation result for a bone portion included in the first and second radiographic images G1 and G2 and the third and fourth radiographic images G3 and G4 on the basis of these images. In this embodiment, the first to fourth radiographic images G1 to G4 are the radiographic images of the chest and abdomen of the subject H and include vertebrae. It is assumed that the radiographic image processing device 10 according to this embodiment derives an evaluation result for a vertebral body included in the vertebrae as the evaluation result for the bone portion.

Figure 3:
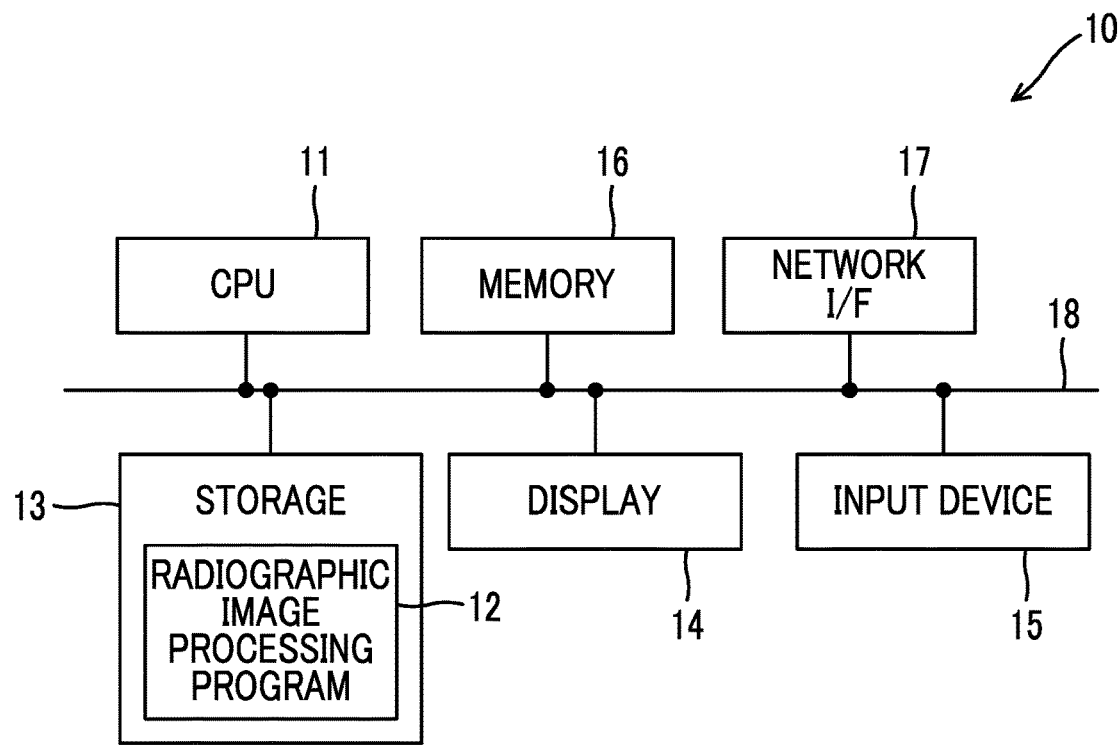
FIG. 3 is a diagram schematically illustrating a configuration of the radiographic image processing device according to this embodiment of the present disclosure.

Next, the radiographic image processing device according to this embodiment will be described. First, the hardware configuration of the radiographic image processing device according to this embodiment will be described with reference to FIG. 3. As illustrated in FIG. 3, the radiographic image processing device 10 is a computer, such as a workstation, a server computer, or a personal computer, and comprises a central processing unit (CPU) 11, a non-volatile storage 13, and a memory 16 as a temporary storage area. In addition, the radiographic image processing device 10 comprises a display 14, such as a liquid crystal display, an input device 15, such as a keyboard and a mouse, and a network interface (I/F) 17 that is connected to an external network (not illustrated). The CPU 11, the storage 13, the display 14, the input device 15, the memory 16, and the network I/F 17 are connected to a bus 18. The CPU 11 is an example of a processor according to the present disclosure.

The storage 13 is implemented by, for example, a hard disk drive (HDD), a solid state drive (SSD), and a flash memory. A radiographic image processing program 12 installed in the radiographic image processing device 10 is stored in the storage 13 as a storage medium. The CPU 11 reads the radiographic image processing program 12 from the storage 13, expands the radiographic image processing program 12 in the memory 16, and executes the expanded radiographic image processing program 12.

In addition, the radiographic image processing program 12 is stored in a storage device of a server computer connected to the network or a network storage so as to be accessed from the outside and is downloaded and installed in the computer forming the radiographic image processing device 10 on demand. Alternatively, the radiographic image processing program 12 is recorded on a recording medium, such as a digital versatile disc (DVD) or a compact disc read only memory (CD-ROM), is distributed, and is installed in the computer forming the radiographic image processing device 10 from the recording medium.

Figure 4:
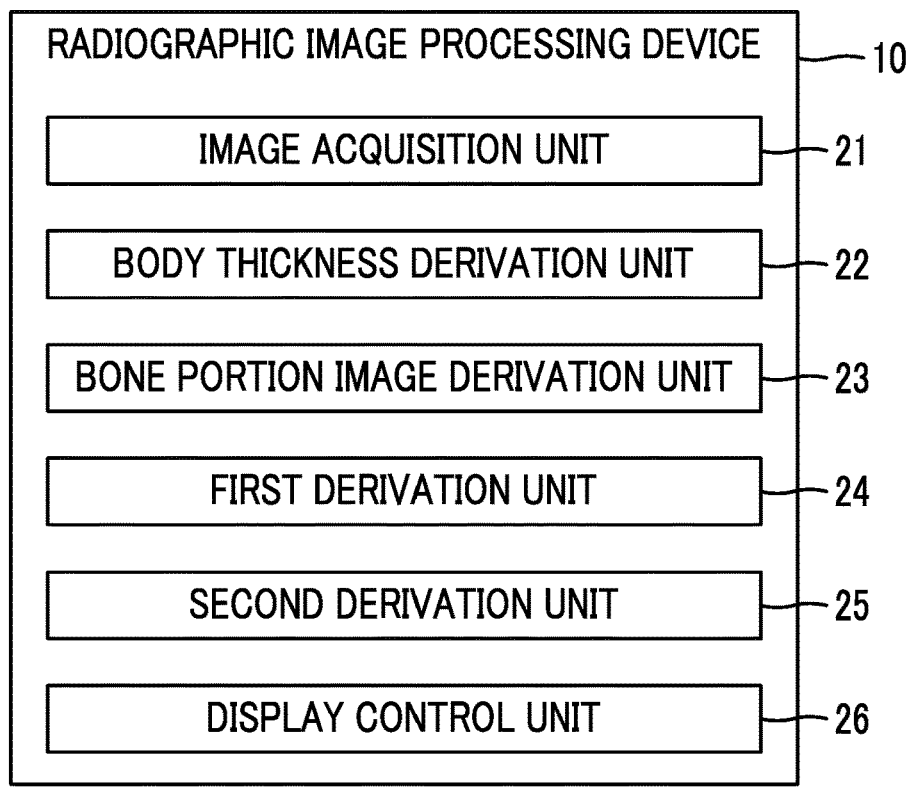
FIG. 4 is a diagram illustrating a functional configuration of the radiographic image processing device according to this embodiment of the present disclosure.

Next, the functional configuration of the radiographic image processing device according to this embodiment will be described. FIG. 4 is a diagram illustrating the functional configuration of the radiographic image processing device according to this embodiment. As illustrated in FIG. 4, the radiographic image processing device 10 comprises an image acquisition unit 21, a body thickness derivation unit 22, a bone portion image derivation unit 23, a first derivation unit 24, a second derivation unit 25, and a display control unit 26. Then, the CPU 11 executes the radiographic image processing program 12 to function as the image acquisition unit 21, the body thickness derivation unit 22, the bone portion image derivation unit 23, the first derivation unit 24, the second derivation unit 25, and the display control unit 26.

The image acquisition unit 21 directs the imaging apparatus 1 to capture the image of the subject H and acquires the first radiographic image G1 and the second radiographic image G2, which are the front images of the chest and abdomen of the subject H, and the third radiographic image G3 and the fourth radiographic image G4, which are the side images of the chest and abdomen of the subject H, from the first and second radiation detectors 5 and 6. In a case in which the first and second radiographic images G1 and G2 and the third and fourth radiographic images G3 and G4 are acquired, imaging conditions, such as an irradiation dose of radiation, a tube voltage, and a source-to-image receptor distance (SID), are set. The set imaging conditions are stored in the storage 13.

Here, the first to fourth radiographic images G1 to G4 include the scattered ray components generated by the scattering of the X-rays emitted to the subject H by the subject H. Therefore, in this embodiment, the bone portion image derivation unit 23, which will be described below, removes the scattered ray components from the first to fourth radiographic images G1 to G4. The body thickness distribution of the subject H is required to remove the scattered ray components. For this purpose, the body thickness derivation unit 22 derives the body thickness distribution (x, y) of the subject H at each pixel position (x, y) of the radiographic images. In this embodiment, the first and second radiographic images G1 and G2 which are the front images of the subject H and the third and fourth radiographic images G3 and G4 which are the side images of the subject H are acquired. Therefore, in this embodiment, the body thickness derivation unit 22 derives a first body thickness distribution $T1(x, y)$ in the front-back direction of the subject H in the front-back direction on the basis of the first and second radiographic images G1 and G2 which are the front images of the subject H. In addition, the body thickness derivation unit 22 derives a second body thickness distribution $T2(x, y)$ of the subject H in the left-right direction on the basis of the third and fourth radiographic images G3 and G4 which are the side images of the subject H.

First, the derivation of the first body thickness distribution $T1(x, y)$ of the subject H in the front-back direction will be described. In this embodiment, the body thickness derivation unit 22 uses the first radiographic image G1 acquired by the first radiation detector 5 closer to the subject H in a case in which the first body thickness distribution $T1(x, y)$ of the subject H is derived. However, the second radiographic image G2 acquired by the second radiation detector 6 farther from the subject H may be used. In addition, weighting and subtraction may be performed between the corresponding pixels of the first radiographic image G1 and the second radiographic image G2 to generate a soft portion image in which a soft portion of the subject H included in each radiographic image has been highlighted. Then, the first body thickness distribution $T1(x, y)$ of the subject H may be derived using the soft portion image. Further, even in a case in which any of the images is used, a low-frequency image indicating a low-frequency component of the image may be generated, and the first body thickness distribution $T1(x, y)$ may be derived using the low-frequency image.

The body thickness derivation unit 22 may derive the first body thickness distribution $T1(x, y)$ of the subject H using, for example, the method disclosed in JP2015-043959A. Hereinafter, an example of a method for deriving the first body thickness distribution $T1(x, y)$ of the subject H will be described.

First, the body thickness derivation unit 22 acquires a virtual model K1 of the subject H having an initial body thickness distribution $Ts1(x, y)$. The virtual model K1 is data which virtually indicates the subject H and in which the body thickness according to the initial body thickness distribution $Ts1(x, y)$ is associated with the coordinate position of each pixel of the first radiographic image G1. In addition, the virtual model K1 of the subject H having the initial body thickness distribution $Ts1(x, y)$ is stored in the storage 13 in advance. However, the virtual model K1 may be acquired from an external server storing the virtual model K1.

Then, the body thickness derivation unit 22 derives an estimated primary ray image $Ip1(x, y)$ which is obtained by estimating a primary ray image obtained by capturing the image of the virtual model K1 and an estimated scattered ray image $Is1(x, y)$ which is obtained by estimating a scattered ray image obtained by capturing the image of the virtual model K1, on the basis of the virtual model K1, as represented by the following Expressions (1) and (2). Further, as represented by the following Expression (3), the body thickness derivation unit 22 derives a composite image of the estimated primary ray image $Ip1(x, y)$ and the estimated scattered ray image $Is1(x, y)$ as an estimated image $Im1(x, y)$ which is obtained by estimating the first radiographic image G1 obtained by capturing the image of the subject H.

$$Ip1(x,y) = Io(x,y) \times \exp(-\mu \times T1(x,y)) \quad (1)$$

$$Is1(x,y) = Io(x,y) * S\sigma(T1(x,y)) \quad (2)$$

$$Im1(x,y) = Is1(x,y) + Ip1(x,y) \quad (3)$$

Here, (x, y) is the coordinate of the pixel position of the first radiographic image G1, $Ip(x, y)$ is a primary ray component at the pixel position (x, y), $Is(x, y)$ is a scattered ray component at the pixel position (x, y), $Io(x, y)$ is an incident dose on the surface of the subject H at the pixel position (x, y), $\mu$ is an X-ray attenuation coefficient of the subject H, and Sσ(T1(x, y)) is a convolutional kernel indicating scattering characteristics corresponding to the first body thickness distribution T1(x, y) of the subject H at the pixel position (x, y). In addition, in the first derivation of the estimated image Im1(x, y), the initial body thickness distribution Ts1(x, y) is used as the body thickness distribution T1(x, y) in Expressions (1) and (2). Expression (1) is based on a known exponential attenuation law, and Expression (2) is based on the method disclosed in "J M Boon et al, An analytical model of the scattered radiation distribution in diagnostic radiology, Med. Phys. 15(5), September/October 1988 (Reference Literature 1). Further, the incident dose Io(x, y) on the surface of the subject H is an irradiation dose that is derived on the basis of the imaging conditions. Furthermore, an X-ray attenuation coefficient of the soft tissue of the subject H may be used as the X-ray attenuation coefficient of the subject H.

In addition, * in Expression (2) is an operator indicating a convolution operation. The properties of the kernel change depending on, for example, the distribution of the irradiation field, the distribution of the composition of the subject H, the irradiation dose at the time of imaging, the tube voltage, the imaging distance, and the characteristics of the radiation detectors 5 and 6, in addition to the body thickness of subject H. According to the method disclosed in Reference Literature 1, the scattered rays can be approximated by the convolution of a point spread function (Sσ(T1(x, y))) in Expression (3)) for the primary rays. In addition, Sσ(T1(x, y)) can be experimentally calculated according to, for example, irradiation field information, subject information, and imaging conditions.

In this embodiment, Sσ(T1(x, y)) may be calculated on the basis of irradiation field information, subject information, and imaging conditions at the time of imaging. However, a table in which various types of irradiation field information, various types of subject information, various imaging conditions, and Sσ(T1(x, y)) are associated with each other may be stored in the storage 13, and Sσ(T1(x, y)) may be calculated on the basis of the irradiation field information, the subject information, and the imaging conditions at the time of imaging with reference to the table. In addition, Sσ(T1(x, y)) may be approximated by T1(x, y).

Then, the body thickness derivation unit 22 corrects the initial body thickness distribution Ts1(x, y) of the virtual model K1 such that the difference between the estimated image Im1 and the first radiographic image G1 is reduced. The body thickness derivation unit 22 repeats the generation of the estimated image Im1 using the corrected first body thickness distribution T1(x, y) and the correction of the first body thickness distribution T1(x, y) until the difference between the estimated image Im1 and the first radiographic image G1 satisfies a predetermined end condition. The body thickness derivation unit 22 derives the body thickness distribution in a case in which the end condition is satisfied as the first body thickness distribution T1(x, y) in the front image of the subject H.

Figure 5:
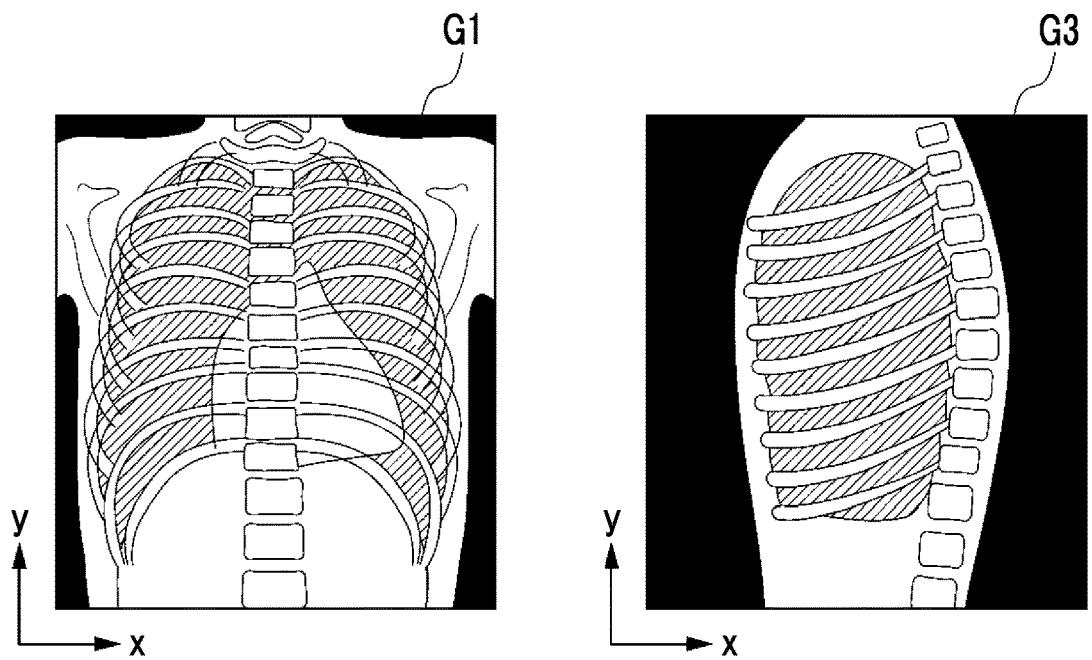
FIG. 5 is a diagram illustrating a first radiographic image which is a front image and a third radiographic image which is a side image side by side.

However, since the cross section of the subject H perpendicular to the body axis has a shape close to an elliptical shape, the place where the first body thickness distribution T1(x, y) is maximized in the first radiographic image G1 is the vertebral body. Since the vertebral body is a bone tissue and has a larger X-ray attenuation than a soft tissue, the derived first body thickness distribution T1(x, y) is likely to be larger than the actual body thickness in the vertebral body. Here, in this embodiment, the third and fourth radiographic images G3 and G4 which are the side images of the subject H are acquired. FIG. 5 is a diagram illustrating the first radiographic image G1 which is a front image and the third radiographic image G3 which is a side image side by side. As illustrated in FIG. 5, in a case in which the first body thickness distribution T1(x, y) is derived, the maximum value of the body thickness of the subject H in the front-back direction at the same position in the y direction is known from the third radiographic image G3. On the contrary, in a case in which the second body thickness distribution T2(x, y) which will be described below is derived, the maximum value of the body thickness of the subject H in the left-right direction at the same position in the y direction is known from the first radiographic image G1. Further, in FIG. 5, x and y indicate the two-dimensional coordinates of the first radiographic image G1 and the third radiographic image G3.

Therefore, in this embodiment, the body thickness derivation unit 22 limits the value of the corrected first body thickness distribution T1(x, y) so as to be equal to or less than the maximum value of the body thickness of the subject H at the same position in the y direction which is measured in the third radiographic image G3 in a case in which the first body thickness distribution T1(x, y) is derived. This makes it possible to improve the accuracy of deriving the first body thickness distribution T1(x, y). Further, it is possible to reduce the processing time required to derive the first body thickness distribution T1(x, y).

Next, the derivation of the second body thickness distribution T2(x, y) of the subject H in the left-right direction will be described. In this embodiment, the body thickness derivation unit 22 uses the third radiographic image G3 acquired by the first radiation detector 5 closer to the subject H in a case in which the second body thickness distribution T2(x, y) of the subject H is derived. However, the fourth radiographic image G4 acquired by the second radiation detector 6 farther from the subject H may be used. In addition, weighting and subtraction may be performed between the corresponding pixels of the third radiographic image G3 and the fourth radiographic image G4 to generate a soft portion image in which a soft portion of the subject H included in each radiographic image has been highlighted, and the second body thickness distribution T2(x, y) of the subject H may be derived using the soft portion image. Further, even in a case in which any of the images is used, a low-frequency image indicating a low-frequency component of the image may be generated, and the second body thickness distribution T2(x, y) may be derived using the low-frequency image.

First, in a case in which the second body thickness distribution T2(x, y) is derived, the body thickness derivation unit 22 acquires a virtual model K2 of the subject H having an initial body thickness distribution Ts2(x, y). The virtual model K2 is data which virtually indicates the subject H and in which the body thickness according to the initial body thickness distribution Ts2(x, y) is associated with the coordinate position of each pixel of the third radiographic image G3. In addition, the virtual model K2 of the subject H having the initial body thickness distribution Ts2(x, y) is stored in the storage 13 in advance. However, the virtual model K2 may be acquired from an external server storing the virtual model K2.

Then, the body thickness derivation unit 22 derives an estimated primary ray image Ip2(x, y) which is obtained by estimating a primary ray image obtained by capturing the image of the virtual model K2 and an estimated scattered ray image Is2(x, y) which is obtained by estimating a scattered ray image obtained by capturing the image of the virtual model K2, on the basis of the virtual model K2, as represented by the following Expressions (4) and (5). Further, as represented by the following Expression (6), the body thickness derivation unit 22 derives a composite image of the estimated primary ray image Ip2(x, y) and the estimated scattered ray image Is2(x, y) as an estimated image Im2(x, y) which is obtained by estimating the third radiographic image G3 obtained by capturing the image of the subject H. In addition, arithmetic expressions and coefficients in Expressions (4) to (6) are the same as those in Expressions (1) to (3).

$$Ip2(x,y)=Io(x,y)\times \exp(-\mu \times T2(x,y)) \quad (4)$$

$$Is2(x,y)=Io(x,y)*S\sigma(T2(x,y)) \quad (5)$$

$$Im2(x,y)=Is2(x,y)+Ip2(x,y) \quad (6)$$

Then, the body thickness derivation unit 22 corrects the initial body thickness distribution Ts2(x, y) of the virtual model K2 such that the difference between the estimated image Im2 and the third radiographic image G3 is reduced. The body thickness derivation unit 22 repeats the generation of the estimated image Im2 using the corrected second body thickness distribution T2(x, y) and the correction of the second body thickness distribution T2(x, y) until the difference between the estimated image Im2 and the third radiographic image G3 satisfies a predetermined end condition. The body thickness derivation unit 22 derives the body thickness distribution in a case in which the end condition is satisfied as the second body thickness distribution T2(x, y) in the side image of the subject H.

Here, the body thickness derivation unit 22 limits the value of the corrected second body thickness distribution T2(x, y) so as to be equal to or less than the maximum value of the body thickness of the subject H at the same position in the y direction which is measured in the first radiographic image G1 in a case in which the second body thickness distribution T2(x, y) is derived. This makes it possible to improve the accuracy of deriving the second body thickness distribution T2(x, y). Further, it is possible to reduce the processing time required to derive the second body thickness distribution T2(x, y).

On the other hand, in this embodiment, since the front and side images of the subject H are used, the thickness of the vertebral body of the subject H in the front-back direction can be derived from the third radiographic image G3 or the fourth radiographic image G4 which is a side image. Further, the thickness of the vertebral body of the subject H in the left-right direction can be derived from the first radiographic image G1 or the second radiographic image G2 which is a front image. Here, since the vertebral body has a larger size than the rib and the like, a value considering the thickness of the vertebral body is used as the X-ray attenuation coefficient in Expression (1), which makes it possible to derive the estimated primary ray images Ip1(x, y) and Ip2(x, y), the estimated scattered ray images Is1(x, y) and Is2(x, y), and the body thickness distributions T1(x, y) and T2(x, y) with higher accuracy.

Therefore, in a case in which the first body thickness distribution T1(x, y) is derived, a thickness Tb1(x, y) of the vertebral body in the front-back direction in the third radiographic image G3 or the fourth radiographic image G4 may be derived, an X-ray attenuation coefficient μt1(x, y) may be derived by the following Expression (7), and the derived X-ray attenuation coefficient μt1(x, y) may be applied to Expression (1) to derive the estimated primary ray image Ip1(x, y). In addition, in a case in which the second body thickness distribution T2(x, y) is derived, a thickness Tb2(x, y) of the vertebral body in the left-right direction in the first radiographic image G1 or the second radiographic image G2 may be derived, an X-ray attenuation coefficient μt2(x, y) may be derived by the following Expression (8), and the derived X-ray attenuation coefficient μt2(x, y) may be applied to Expression (4) to derive the estimated primary ray image Ip2(x, y). Further, in Expressions (7) and (8), μs is an X-ray attenuation coefficient of a soft tissue, and μb is an X-ray attenuation coefficient of a bone tissue.

$$\mu t1(x,y)=\{\mu b\times Tb1(x,y)+\mu s\times (T1(x,y)-Tb1(x,y)\}/T1(x,y) \quad (7)$$

$$\mu t2(x,y)=\{\mu b\times Tb2(x,y)+\mu s\times (T2(x,y)-Tb2(x,y)\}/T2(x,y) \quad (8)$$

The bone portion image derivation unit 23 derives a first bone portion image Gb1 in which the bone portion has been highlighted in the front image of the subject H from the first radiographic image G1 and the second radiographic image G2. The bone portion image derivation unit 23 derives a second bone portion image Gb2 in which a bone portion has been highlighted in the side image of the subject H from the third radiographic image G3 and the fourth radiographic image G4. In a case in which the first bone portion image Gb1 and the second bone portion image Gb2 are derived, the bone portion image derivation unit 23 removes scattered ray components from the first to fourth radiographic images G1 to G4.

In a case in which the scattered ray components are removed from the first radiographic image G1, the bone portion image derivation unit 23 derives the estimates scattered ray image Is1(x, y) on the basis of the first body thickness distribution T1(x, y) using Expression (2). Then, the bone portion image derivation unit 23 subtracts the estimated scattered ray image Is1(x, y) from the first radiographic image G1 to remove the scattered ray components from the first radiographic image G1. On the other hand, in a case in which the scattered ray components are removed from the second radiographic image G2, the bone portion image derivation unit 23 subtracts the estimated scattered ray image Is1(x, y) derived by Expression (2) from the second radiographic image G2 to remove the scattered ray components from the second radiographic image G2. In this case, the bone portion image derivation unit 23 may multiply the estimated scattered ray image Is1(x, y) by a coefficient considering the attenuation of X-rays by the first radiation detector 5 and the X-ray energy conversion filter 7 and may subtract the estimated scattered ray image Is1(x, y) multiplied by the coefficient from the second radiographic image G2.

On the other hand, in a case in which the scattered ray components are removed from the third radiographic image G3, the bone portion image derivation unit 23 derives the estimates scattered ray image Is2(x, y) on the basis of the second body thickness distribution T2(x, y) using Expression (5). Then, the bone portion image derivation unit 23 subtracts the estimated scattered ray image Is2(x, y) from the third radiographic image G3 to remove the scattered ray components from the third radiographic image G3. On the other hand, in a case in which the scattered ray components are removed from the fourth radiographic image G4, the bone portion image derivation unit 23 subtracts the estimated scattered ray image Is2(x, y) derived by Expression (5) from the fourth radiographic image G4 to remove the scattered ray components from the fourth radiographic image G4. In this case, the bone portion image derivation unit 23 may multiply the estimated scattered ray image Is2(x, y) by a coefficient considering the attenuation of X-rays by the first radiation detector 5 and the X-ray energy conversion filter 7 and may subtract the estimated scattered ray image Is2(x, y) multiplied by the coefficient from the fourth radiographic image G4.

Then, the bone portion image derivation unit 23 performs weighting and subtraction between the corresponding pixels of the first radiographic image G1 and the second radiographic image G2, from which the scattered ray components have been removed, to derive the first bone portion image Gb1, as represented by, for example, the following Expression (9). In addition, the bone portion image derivation unit 23 derives the second bone portion image Gb2 in which the bone portion has been highlighted in the side image of the subject H from the third radiographic image G3 and the fourth radiographic image G4 from which the scattered ray components have been removed. Specifically, the bone portion image derivation unit 23 performs weighting and subtraction between the corresponding pixels of the third radiographic image G3 and the fourth radiographic image G4, from which the scattered ray components have been removed, to derive the second bone portion image Gb2, as represented by, for example, the following Expression (10). In Expressions (9) and (10), w1 and w2 are weighting coefficients, and x and y are the coordinates of each pixel of the first bone portion image Gb1 and the second bone portion image Gb2.

$$Gb1(x,y)=G1(x,y)-w1 \times G2(x,y) \quad (9)$$

$$Gb2(x,y)=G3(x,y)-w2 \times G4(x,y) \quad (10)$$

The first derivation unit 24 derives a bone mineral content for each pixel in the bone portion included in each of the first-direction radiographic image and the second-direction radiographic image. That is, the first derivation unit 24 derives bone mineral contents B1 and B2 for each pixel of the bone portion included in the first bone portion image Gb1 and the second bone portion image Gb2. In this embodiment, the first derivation unit 24 converts each pixel value of the first bone portion image Gb1 and the second bone portion image Gb2 into the pixel value of the bone image acquired under the reference imaging conditions to derive the bone mineral contents B1 and B2. Specifically, the first derivation unit 24 corrects each pixel value of the first bone portion image Gb1 and the second bone portion image Gb2 using a correction coefficient acquired from a look-up table, which will be described below, to derive the bone mineral contents B1 and B2.

Here, as the tube voltage of the X-ray source 3 and the energy of the X-rays emitted from the X-ray source 3 become higher, the contrast of a soft portion and a bone portion in the radiographic image becomes smaller. Further, in the process of transmitting X-rays through the subject H, beam hardening occurs in which a low energy component of the X-rays is absorbed by the subject H and the energy of the X-rays increases. The increase in the energy of the X-rays due to the beam hardening becomes more significant as the body thickness of the subject H becomes larger.

Figure 6:
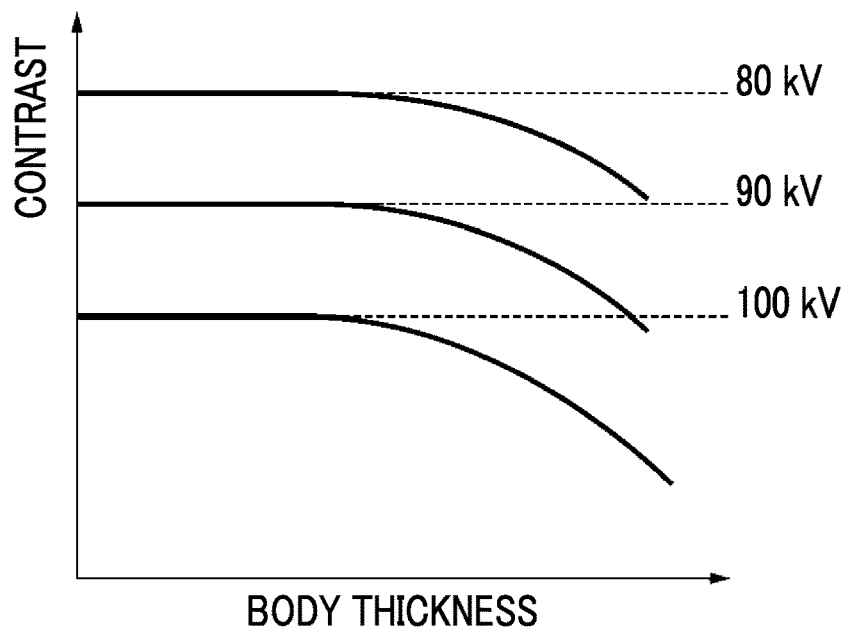
FIG. 6 is a diagram illustrating a relationship between the contrast of a bone portion and a soft portion and a body thickness of the subject.

FIG. 6 is a diagram illustrating the relationship between the contrast of a bone portion and a soft portion and the body thickness of the subject H. In addition, FIG. 6 illustrates the relationship between the contrast of the bone portion and the soft portion and the body thickness of the subject H at three tube voltages of 80 kV, 90 kV, and 100 kV. As illustrated in FIG. 6, the tube voltage becomes higher, the contrast becomes lower. Further, in a case in which the body thickness of the subject H is greater than a certain value, as the body thickness becomes larger, the contrast becomes lower. In addition, as the pixel value of a bone region in the first bone portion image Gb1 and the second bone portion image Gb2 becomes larger, the contrast of the bone portion and the soft portion becomes higher. Therefore, the relationship illustrated in FIG. 6 shifts to the higher contrast side as the pixel value of the bone region in the first bone portion image Gb1 and the second bone portion image Gb2 becomes larger.

In this embodiment, a look-up table for acquiring a correction coefficient for correcting a difference in contrast corresponding to the tube voltage at the time of imaging and a reduction in contrast due to the influence of beam hardening in the first bone portion image Gb1 and the second bone portion image Gb2 is stored in the storage 13. The correction coefficient is a coefficient for correcting each pixel value of the first bone portion image Gb1 and the second bone portion image Gb2.

Figure 7:
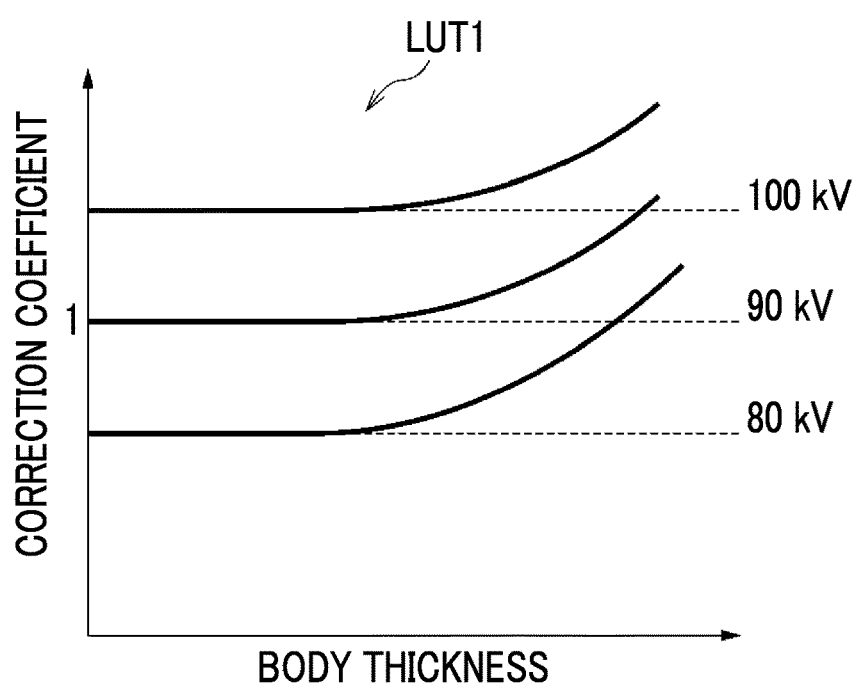
FIG. 7 is a diagram illustrating an example of a look-up table.

FIG. 7 is a diagram illustrating an example of the look-up table. FIG. 7 illustrates a look-up table LUT1 in which the reference imaging condition is set to a tube voltage of 90 kV. As illustrated in FIG. 7, in the look-up table LUT1, as the tube voltage becomes higher and the body thickness of the subject H becomes larger, a larger correction coefficient is set. In the example illustrated in FIG. 7, since the reference imaging condition is a tube voltage of 90 kV, the correction coefficient is 1 in a case in which the tube voltage is 90 kV and the body thickness is 0. In addition, in FIG. 7, the look-up table LUT1 is two-dimensionally illustrated. However, the correction coefficient varies depending on the pixel value of the bone region. Therefore, the look-up table LUT1 is actually a three-dimensional table to which an axis indicating the pixel value of the bone region is added.

The first derivation unit 24 extracts, from the look-up table LUT1, a correction coefficient C0(x, y) for each pixel corresponding to the first body thickness distribution T1(x, y) and the second body thickness distribution T2(x, y) derived by the body thickness derivation unit 22 and the imaging conditions including the set value of the tube voltage stored in the storage 13. Then, as represented by the following Expressions (11) and (12), the first derivation unit 24 multiplies the pixel values Gb1(x, y) and Gb2(x, y) of the bone regions in the first bone portion image Gb1 and the second bone portion image Gb2 by the correction coefficient C0(x, y) to derive the bone mineral contents B1(x, y) and B2(x, y) for each pixel of the first bone portion image Gb1 and the second bone portion image Gb2. The bone mineral contents B1(x, y) and B2(x, y) derived in this way indicate the pixel values of the bone portions of the bone regions included in the radiographic images which have been acquired by capturing the image of the subject H at a tube voltage of 90 kV that is the reference imaging condition and from which the influence of beam hardening has been removed.

$$B1(x,y)=C0(x,y) \times Gb1(x,y) \quad (11)$$

$$B2(x,y)=C0(x,y) \times Gb2(x,y) \quad (12)$$

Figure 8:
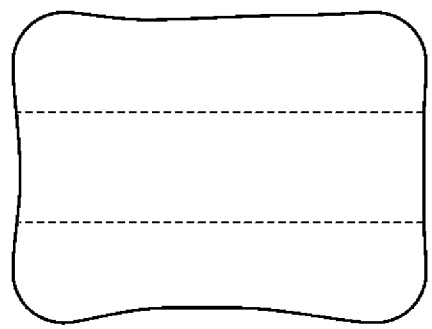
FIG. 8 is a diagram illustrating the division of a vertebral body.
Figure 9:
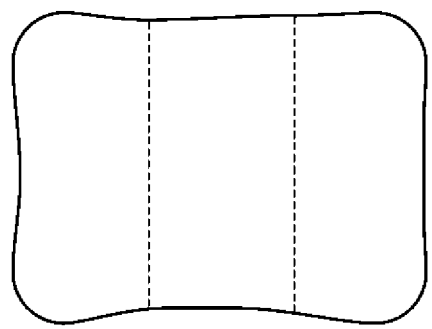
FIG. 9 is a diagram illustrating the division of the vertebral body.
Figure 10:
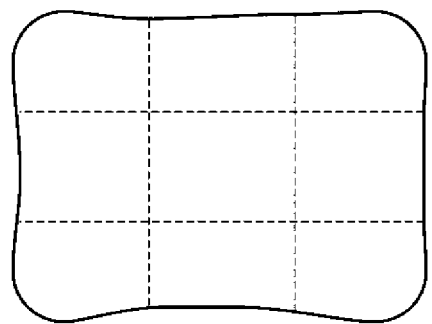
FIG. 10 is a diagram illustrating the division of the vertebral body.

The second derivation unit 25 divides the bone portion included in the first-direction radiographic image into a plurality of small regions and derives a first evaluation result for each small region of the bone portion on the basis of the bone mineral content B1(x, y) derived for the first-direction radiographic image. Further, the second derivation unit 25 divides the bone portion included in the second-direction radiographic image into a plurality of small regions and derives a second evaluation result for each small region of the bone portion on the basis of the bone mineral content B2(x, y) derived for the second-direction radiographic image. Therefore, the second derivation unit 25 divides each vertebral body included in the first bone portion image Gb1 and the second bone portion image Gb2 into small regions. FIG. 8 is a diagram illustrating the division of the vertebral body. In addition, in FIG. 8, only one vertebral body in the first bone portion image Gb1 is illustrated for the sake of explanation. However, the vertebral body in the second bone portion image Gb2 can be similarly divided. As illustrated in FIG. 8, the second derivation unit 25 divides the vertebral body into three small regions in the up-down direction. Further, as illustrated in FIG. 9, the vertebral body may be divided into three small regions in the left-right direction. Alternatively, as illustrated in FIG. 10, the vertebral body may be divided into three small regions in the up-down direction and may be divided into three small regions in the left-right direction. The second derivation unit 25 similarly divides the vertebral body included in the second bone portion image Gb2 into small regions. The number of divisions is not limited to 3 and may be any value.

Then, the second derivation unit 25 derives the first evaluation result and the second evaluation result for each of the divided small regions. Specifically, for the first bone portion image Gb1, a representative value of the bone mineral content $B1(x, y)$ is derived as a first evaluation result R1 for each small region. For example, an average value, a median value, a minimum value, or a maximum value can be used as the representative value. Further, for the second bone portion image Gb2, a representative value of the bone mineral content $B2(x, y)$ is derived as a second evaluation result R2 for each small region.

Figure 11:
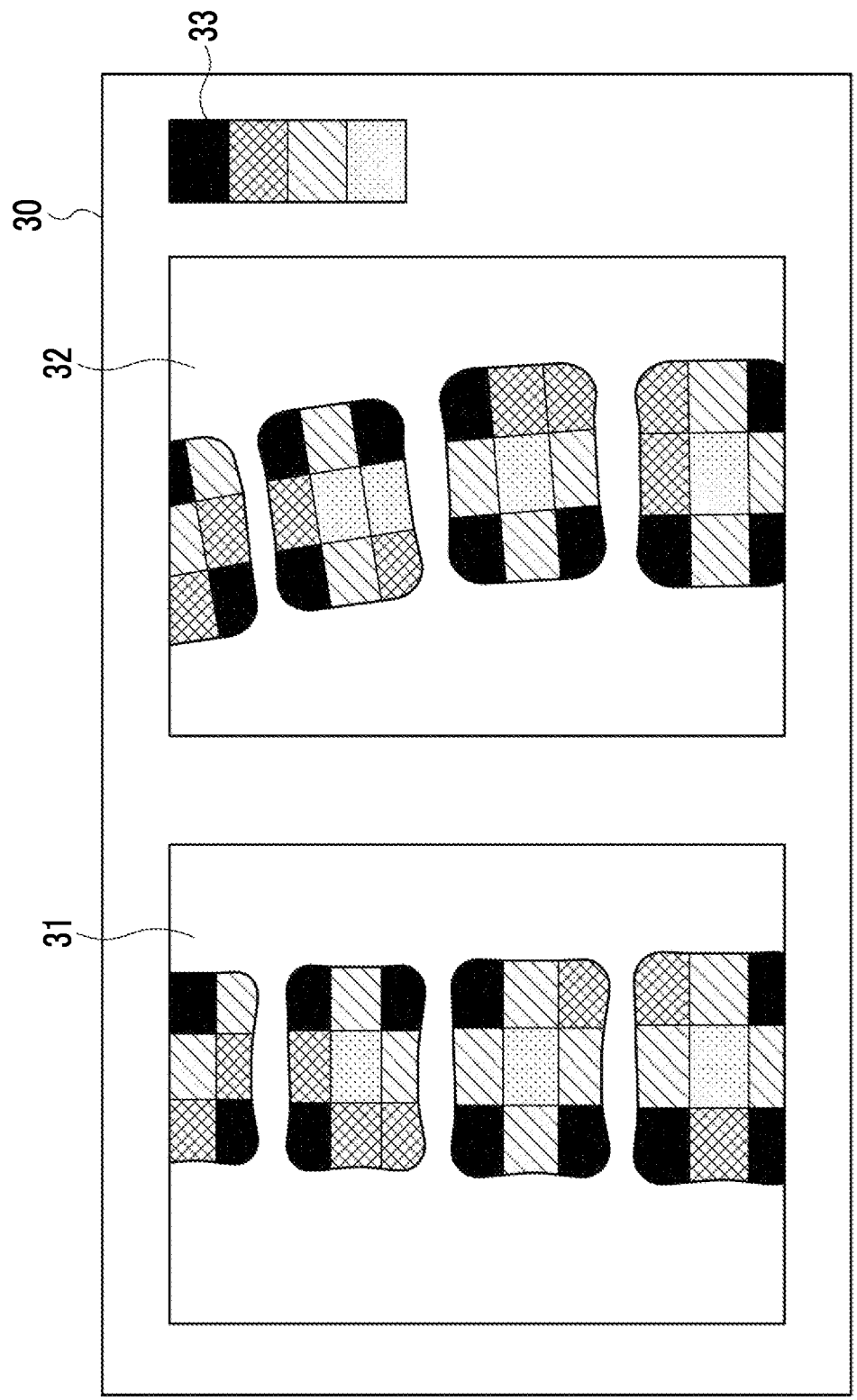
FIG. 11 is a diagram illustrating an evaluation result display screen.

The display control unit 26 displays a display screen including the first evaluation result R1 and the second evaluation result R2 on the display 14. FIG. 11 is a diagram illustrating an evaluation result display screen. As illustrated in FIG. 11, the display control unit 26 displays, on a display screen 30, a mapping image 31 obtained by mapping different colors to the small regions of the first bone portion image Gb1 according to the first evaluation result R1 derived by the second derivation unit 25. Further, the display control unit 26 displays, on the display screen 30, a mapping image 32 obtained by mapping different colors to the small regions of the second bone portion image Gb2 according to the second evaluation result R2 derived by the second derivation unit 25.

In addition, in FIG. 11, for simplicity of explanation, the regions of the corresponding vertebral bodies in the mapping images 31 and 32 are enlarged and displayed. Further, in FIG. 11, the difference between the colors of the bone mineral contents is represented by a difference in hatching. In addition, a reference 33 for representing the bone mineral content is displayed on the display screen 30.

Figure 12:
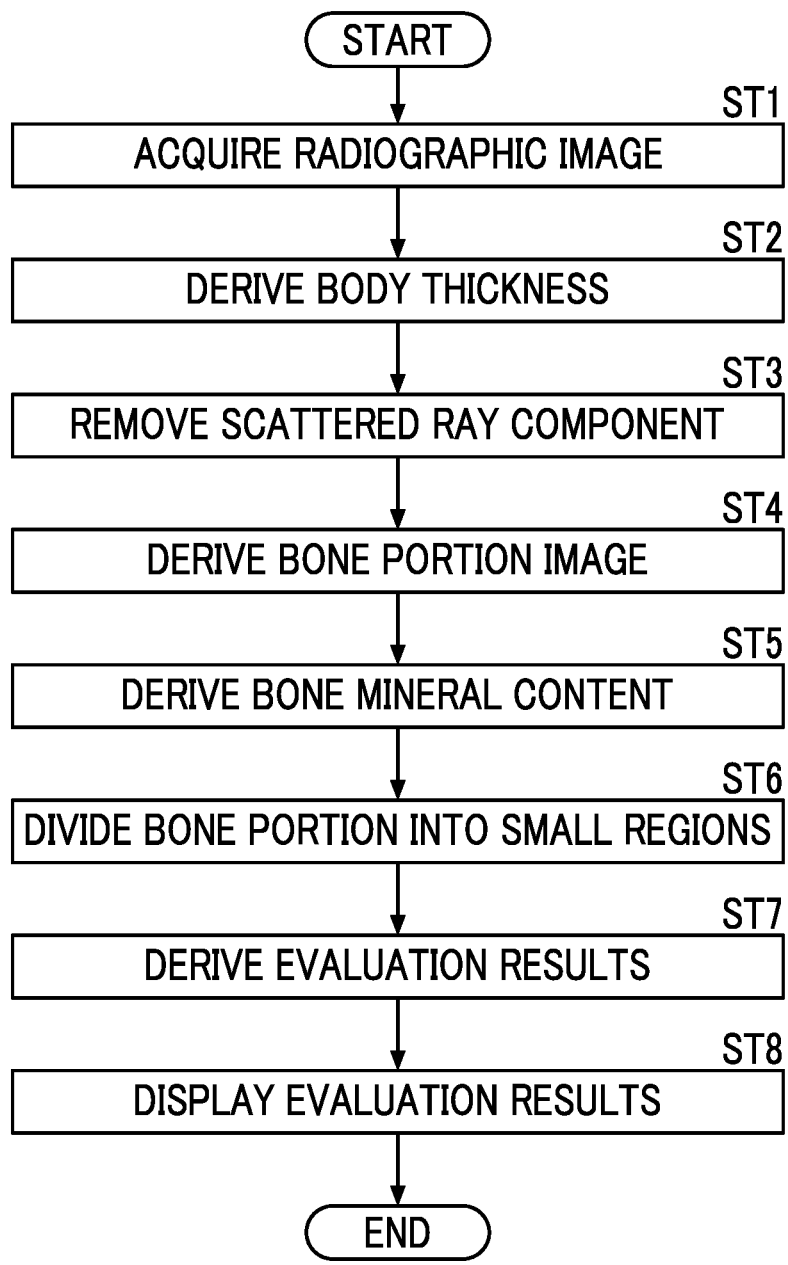
FIG. 12 is a flowchart illustrating a process performed in this embodiment.

Next, a process performed in this embodiment will be described. FIG. 12 is a flowchart illustrating the process performed in this embodiment. In a case in which a process start instruction is input from the input device 15, the process of the radiographic image processing program 12 is started. First, the image acquisition unit 21 causes the imaging apparatus 1 to perform imaging and acquires the first radiographic image G1 and the second radiographic image G2 which are the front images of the subject H and the third radiographic image G3 and the fourth radiographic image G4 which are the side images of the subject H from the first and second radiation detectors 5 and 6 (radiographic image acquisition; Step ST1).

Then, the body thickness derivation unit 22 derives the first body thickness distribution $T1(x, y)$ and the second body thickness distribution $T2(x, y)$ of the subject H (body thickness derivation; Step ST2).

Then, the bone portion image derivation unit 23 removes scattered ray component from the first to fourth radiographic images G1 to G4 (Step ST3) and derives the first bone portion image Gb1 in which the bone portion has been highlighted in the front image of the subject H from the first radiographic image G1 and the second radiographic image G2 from which the scattered ray components have been removed. Further, the bone portion image derivation unit 23 derives the second bone portion image Gb2 in which the bone portion has been highlighted in the side image of the subject H from the third radiographic image G3 and the fourth radiographic image G4 from which the scattered ray components have been removed (bone portion image derivation; Step ST4).

Then, the first derivation unit 24 derives the bone mineral contents B1 and B2 for each pixel in the bone portion included in the first bone portion image Gb1 and the second bone portion image Gb2 (Step ST5). Then, the second derivation unit 25 divides the bone portion included in the first and second bone portion images Gb1 and Gb2 into a plurality of small regions (Step ST6) and derives the first and second evaluation results R1 and R2 for each small region (Step ST7). Further, the display control unit 26 displays a display screen including the first and second evaluation results R1 and R2 on the display 14 (evaluation result display; Step ST8) and ends the process.

As such, in this embodiment, the first bone portion image Gb1 is generated from the first and second radiographic images G1 and G2 acquired on the basis of the first imaging that irradiates the subject H with X-rays in the first direction. In addition, the second bone portion image Gb2 is generated from the third and fourth radiographic images G3 and G4 acquired on the basis of the second imaging that irradiates the subject H with X-rays in the second direction different from the first direction. Then, the bone portion included in the first and second bone portion image Gb1 and Gb2 is divided into small regions, and the first evaluation result R1 and the second evaluation result R2 of the bone mineral contents are derived for each small region. With this configuration, in this embodiment, the first and second evaluation results R1 and R2 are derived using the first and second bone portion images Gb1 and Gb2 acquired by the imaging operations in different directions. Therefore, according to this embodiment, it is possible to understand the three-dimensional state of the bone portion from the first and second evaluation results R1 and R2.

In particular, in this embodiment, the first bone portion image Gb1 is the front image of the subject H, and the second bone portion image Gb2 is the side image of the subject H. Therefore, it is possible to more easily understand the three-dimensional state of the bone portion with reference to the first and second evaluation results R1 and R2.

Further, in this embodiment, since the scattered ray components are removed from the first to fourth radiographic images G1 to G4, it is possible to derive the first and second bone portion images Gb1 and Gb2 that are not affected by the scattered rays. Therefore, the bone mineral contents B1 and B2 and the first and second evaluation results R1 and R2 can be derived so as not to be affected by the scattered rays.

Figure 13:
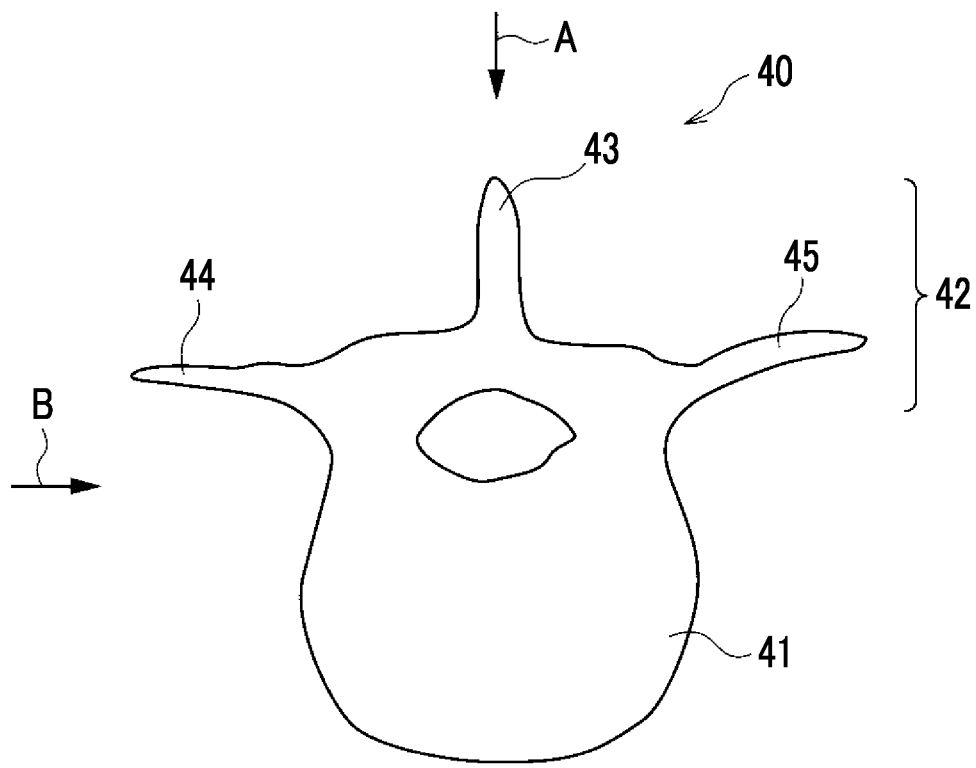
FIG. 13 is a diagram illustrating the structure of a vertebra.

In addition, in this embodiment, the bone mineral content of the vertebral body included in the vertebra is derived. FIG. 13 is a diagram illustrating the structure of the vertebra. As illustrated in FIG. 13, a vertebra 40 includes a vertebral body 41 and a vertebral arch 42. The vertebral arch 42 includes a spinous process 43 and left and right transverse processes 44 and 45. In a case in which the first and second radiographic images G1 and G2 are acquired, the vertebra 40 is irradiated with X-rays in the direction of an arrow A. Therefore, not only the bone mineral content of the vertebral body 41 but also the bone mineral content of the vertebral arch 42 are reflected in the bone mineral content derived from the first bone portion image Gb1. On the other hand, in a case in which the third and fourth radiographic images G3 and G4 are acquired, the vertebra 40 is irradiated with X-rays in the direction of an arrow B. For this reason, the bone mineral content of the vertebral arch 42 is not reflected in the bone mineral content derived from the second bone portion image Gb2, and the bone mineral content of only the vertebral body 41 is reflected in the derived bone mineral content. Therefore, as in this embodiment, the derivation of the bone mineral content from the second bone portion image Gb2 which is the side image of the vertebral body makes it possible to derive the bone mineral content of only the vertebral body 41 without the influence of the vertebral arch 42.

Figure 14:
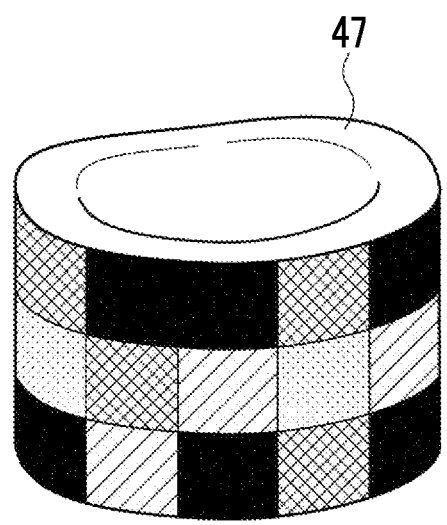
FIG. 14 is a diagram illustrating an evaluation result display screen.

Further, in the above-described embodiment, the display screen 30 including the mapping images 31 and 32 obtained by mapping the first evaluation result R1 and the second evaluation result R2 to the first bone portion image Gb1 and the second bone portion image Gb2, respectively, is displayed on the display 14. However, the display aspect of the first and second evaluation results R1 and R2 is not limited thereto. For example, as illustrated in FIG. 14, a three-dimensional model 47 of the vertebra may be generated, and a mapping image in which colors corresponding to the first evaluation result R1 and the second evaluation result R2 are mapped to the three-dimensional model 47 of the vertebra may be displayed on the display 14. In this case, the three-dimensional model 47 of the vertebra may be created by computer graphics or may be generated from, for example, a CT image of the subject H.

Figure 15:
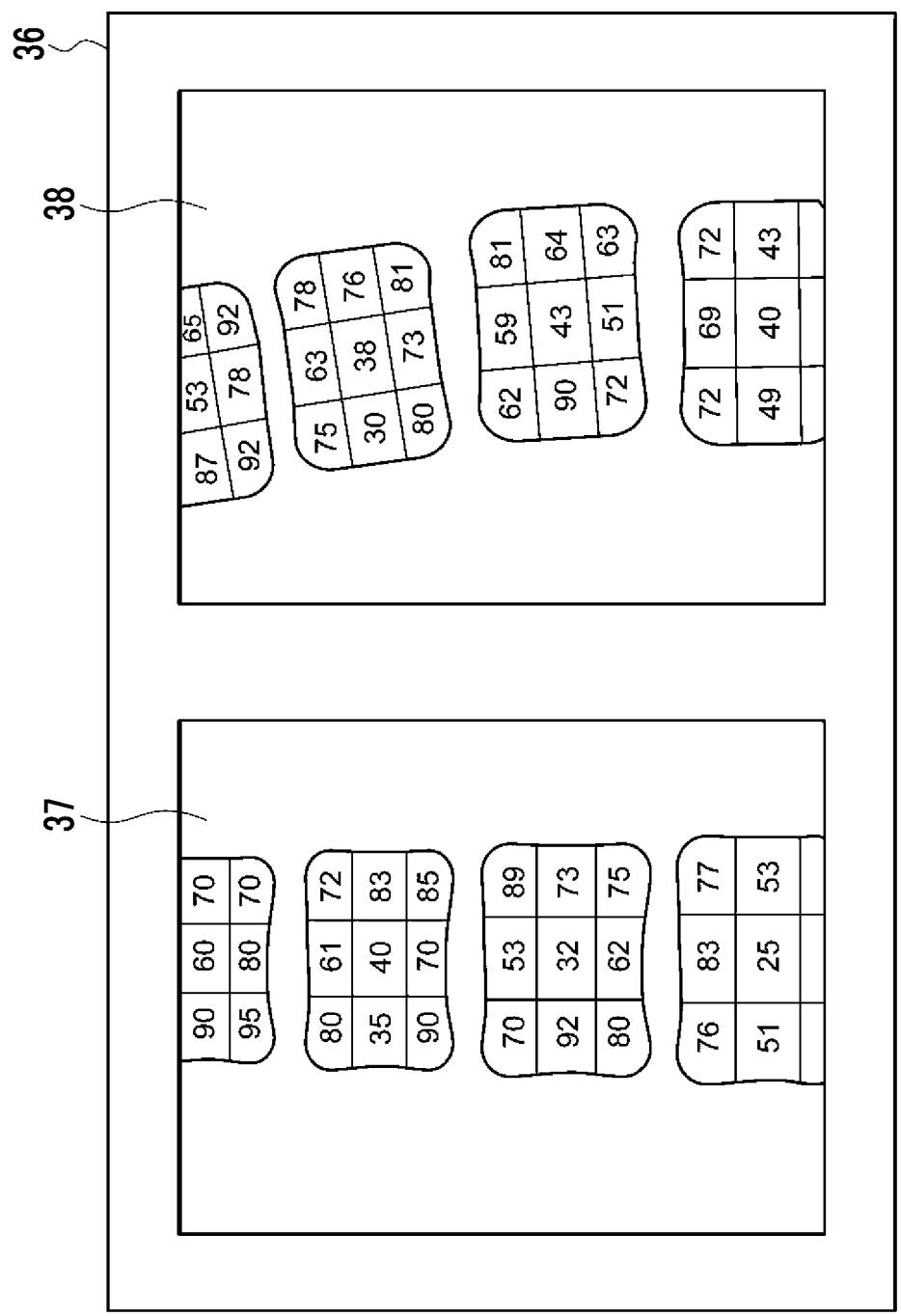
FIG. 15 is a diagram illustrating a display screen of a representative value of a bone mineral content derived for each small region.

Further, in this embodiment, instead of mapping the first and second evaluation results R1 and R2, the representative value of the bone mineral content derived for each small region may be displayed on the display 14. FIG. 15 is a diagram illustrating a display screen of the representative value of the bone mineral content derived for each small region. As illustrated in FIG. 15, an evaluation result image 37 obtained by giving the first evaluation result R1 for each small region as a numerical value to the first bone portion image Gb1 and an evaluation result image 38 obtained by giving the second evaluation result R2 for each small region as a numerical value to the second bone portion image Gb2 are displayed on a display screen 36. Further, in FIG. 15, for simplicity of explanation, the regions of the corresponding vertebral bodies in the evaluation result images 37 and 38 are enlarged and displayed.

Figure 16:
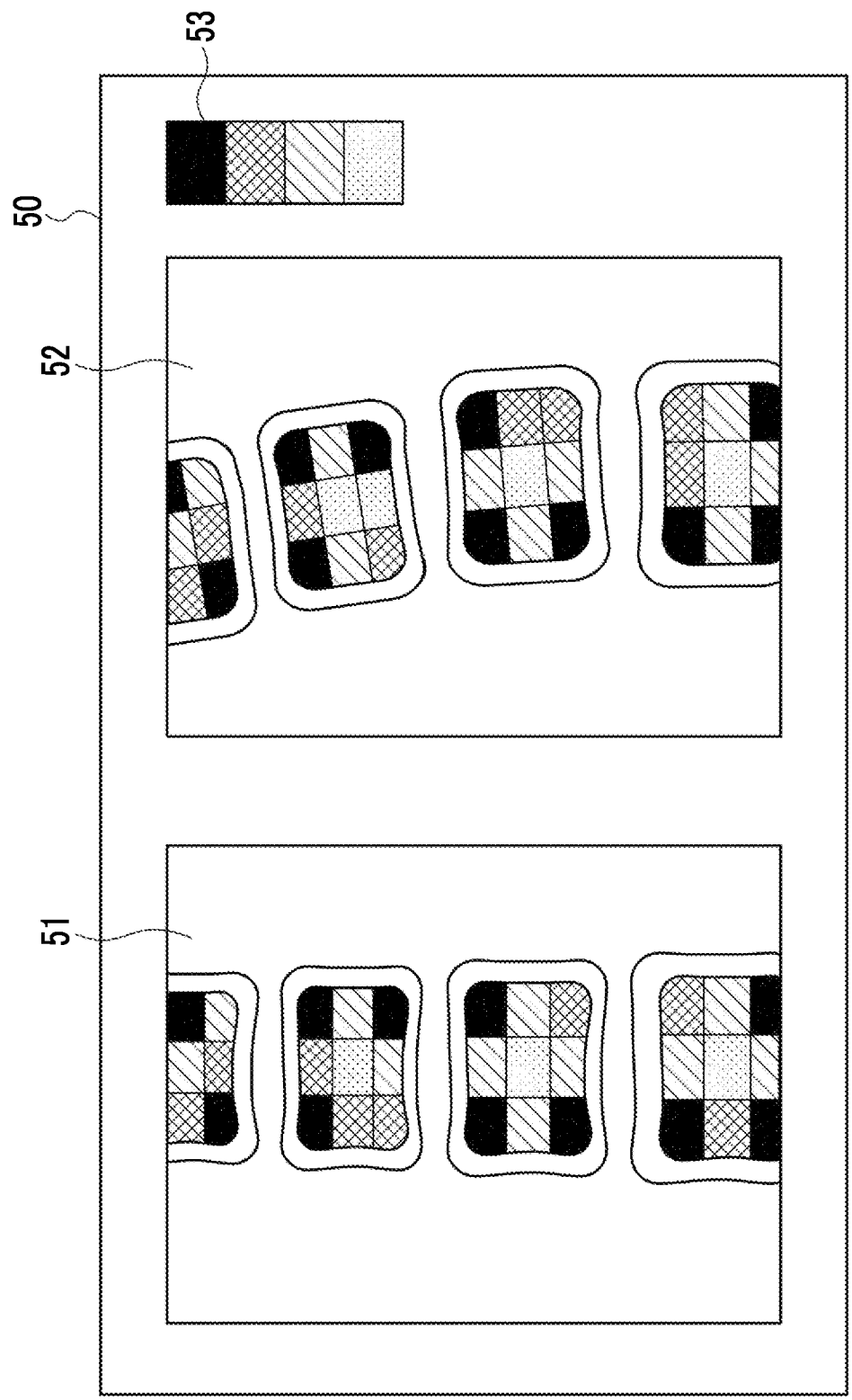
FIG. 16 is a diagram illustrating a display screen of an evaluation result derived only for a cancellous bone region.

In addition, in the above-described embodiment, the entire region of the vertebra in the first and second bone portion images Gb1 and Gb2 is divided into small regions, and the first and second evaluation results R1 and R2 are derived. However, the present disclosure is not limited thereto. Only the cancellous bone region included in the vertebral body may be divided into small regions, and the first and second evaluation results R1 and R2 may be derived. FIG. 16 illustrates a display screen of the evaluation result derived only for the cancellous bone region. As illustrated in FIG. 16, the display control unit 26 displays, on a display screen 50, a mapping image 51 obtained by mapping different colors to the small regions of the cancellous bone in each vertebra of the first bone portion image Gb1 according to the first evaluation result R1 derived by the second derivation unit 25. In addition, the display control unit 26 displays, on the display screen 50, a mapping image 52 obtained by mapping different colors to the small regions of the cancellous bone in each vertebra of the second bone portion image Gb2 according to the second evaluation result R2 derived by the second derivation unit 25.

In addition, in FIG. 16, for simplicity of explanation, the regions of the corresponding vertebral bodies in the mapping images 51 and 52 are enlarged and displayed. Further, in FIG. 16, the difference between the colors of the bone mineral contents is represented by a difference in hatching. In addition, a reference 53 for representing the bone mineral content is displayed on the display screen 50.

Figure 17:
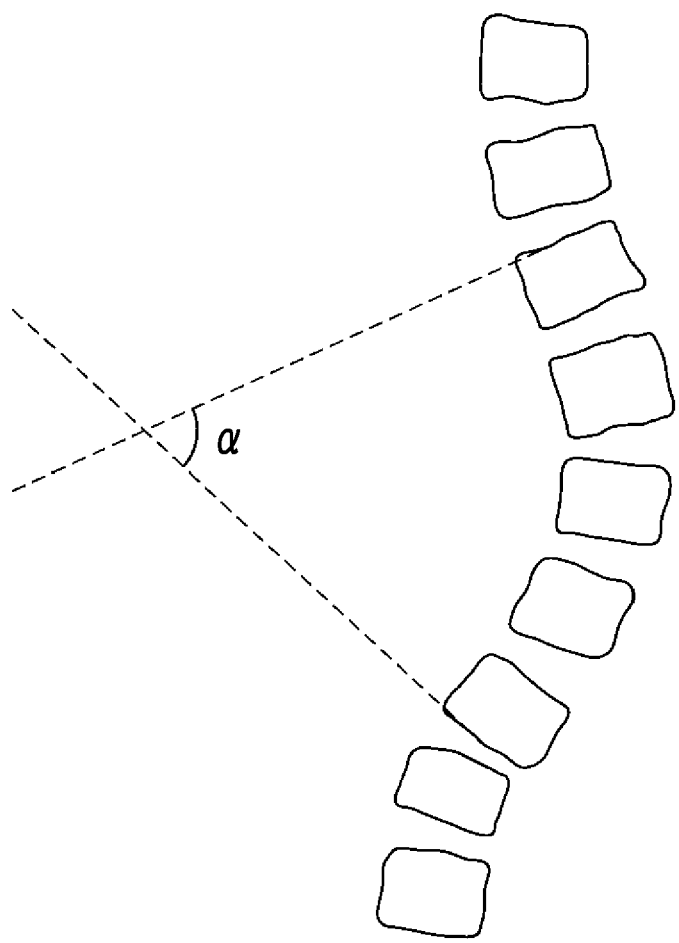
FIG. 17 is a diagram illustrating the derivation of the alignment of the spine in a first bone portion image which is a front image of the subject.

Furthermore, in the above-described embodiment, the second derivation unit 25 may derive information indicating a fracture risk as the first and second evaluation results R1 and R2 on the basis of the alignment of the spine and the bone mineral content of each small region. First, a case in which the bone mineral content derived from the first bone portion image Gb1 is used will be described. FIG. 17 is a diagram illustrating the derivation of the alignment of the spine in the first bone portion image which is the front image of the subject H. In addition, the spine illustrated in FIG. 17 is bent due to scoliosis. As illustrated in FIG. 17, for the front image of the subject H, the second derivation unit 25 calculates a Cobb angle $\alpha$ as the alignment of the spine. Then, the fracture risk of each vertebra is calculated on the basis of the Cobb angle $\alpha$ and the representative value of the bone mineral content for each small region. In addition, in many cases, vertebral body fractures occur in the eleventh thoracic vertebra Th11, the twelfth thoracic vertebra Th12, and the first to fourth lumbar vertebrae L1 to L4. Therefore, the Cobb angle $\alpha$ and the representative value of the bone mineral content may be derived only in these vertebrae. Further, for example, the average value, the median value, the minimum value, or the maximum value of the bone mineral contents derived for each small region of each vertebral body can be used as the representative value of the bone mineral content. However, in this embodiment, it is assumed that the minimum value is used as the representative value of the bone mineral content in order to derive the fracture risk as the evaluation result.

Here, the Cobb angle is an angle of intersection between two straight lines extending from the outer edges of the vertebrae that are inclined at the largest angle above and below the vertebra (apical vertebra) which is the apex of the curve. In addition, the relationship among the Cobb angle $\alpha$, the representative value of the bone mineral content for each small region of the vertebral body, and the fracture risk is determined by a table or an arithmetic expression. The second derivation unit 25 calculates the fracture risk as the first evaluation result R1 from the Cobb angle and the representative value of the bone mineral content for each small region with reference to the table or the arithmetic expression. In this case, the second derivation unit 25 derives the highest fracture risk among the eleventh thoracic vertebra Th11, the twelfth thoracic vertebra Th12, and the first to fourth lumbar vertebrae L1 to L4 as the first evaluation result R1.

Figure 18:
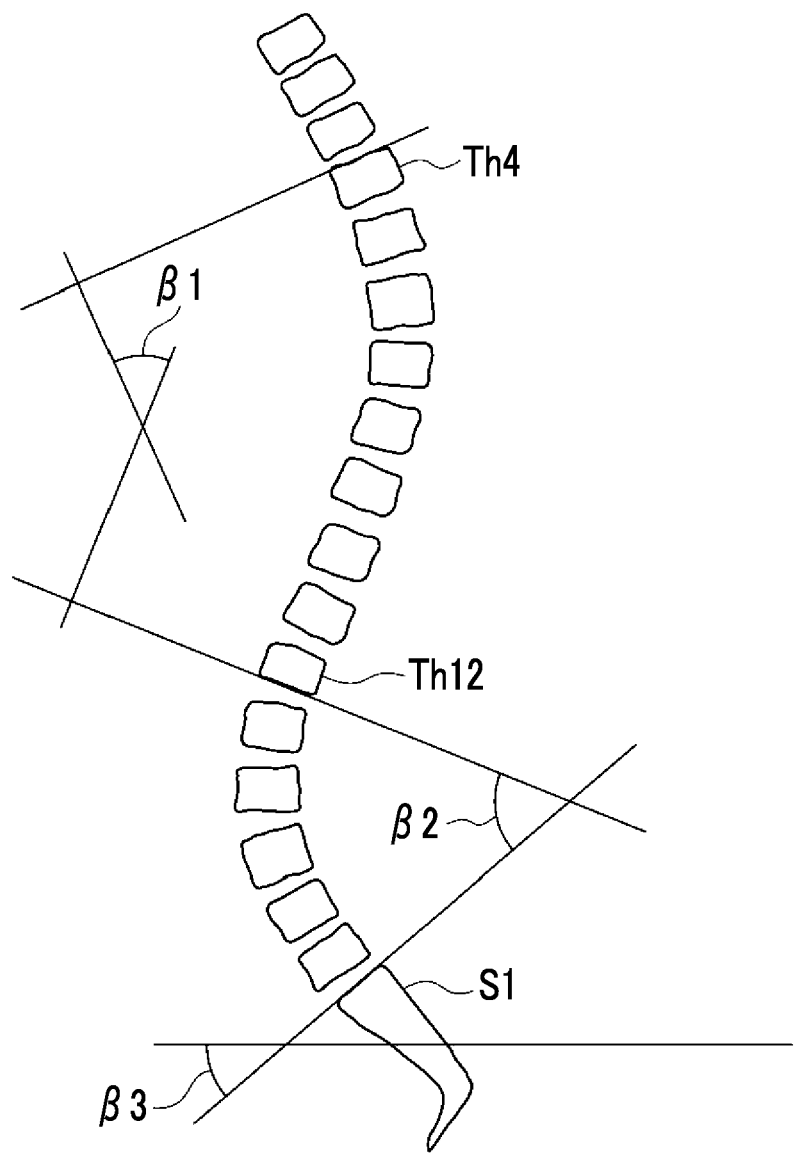
FIG. 18 is a diagram illustrating the derivation of the alignment of the spine in a second bone portion image which is a side image of the subject.

Next, a case in which the bone mineral content derived from the second bone portion image Gb2 is used will be described. FIG. 18 is a diagram illustrating the derivation of the alignment of the spine in the side image of the subject H. For the alignment of the spine in the side image of the subject H, the second derivation unit 25 uses a thoracic kyphosis angle $\beta 1$, a lumbar lordosis angle $\beta 2$, and a sacral slope $\beta 3$. The thoracic kyphosis angle $\beta 1$ is an angle of intersection between two straight lines extending from the upper edge of the fourth thoracic vertebra Th4 and the lower edge of the twelfth thoracic vertebra Th12. The lumbar lordosis angle β2 is an angle of intersection between two straight lines extending from the lower edge of the twelfth thoracic vertebra Th12 and the upper edge of the first sacrum S1. The sacral slope β3 is the angle formed between the upper edge of the first sacrum S1 and a horizontal line. In addition, the relationship among the thoracic kyphosis angle β1, the lumbar lordosis angle β2, the sacral slope β3, the representative value of the bone mineral content for each small region of the vertebral body, and the fracture risk is determined by a table or an arithmetic expression. The second derivation unit 25 calculates the fracture risk as the second evaluation result R2 from the thoracic kyphosis angle β1, the lumbar lordosis angle β2, the sacral slope β3, and the representative values of the bone mineral content of each small region in the vertebral body with reference to the table or the arithmetic expression. In this case, the second derivation unit 25 derives the representative value of the bone mineral content for each small region for the eleventh thoracic vertebra Th11, the twelfth thoracic vertebra Th12, and the first to fourth lumbar vertebrae L1 to L4 and calculates the fracture risk as the second evaluation result R2, using the minimum value among the derived representative values, as in the case of deriving the first evaluation result R1.

Figure 19:
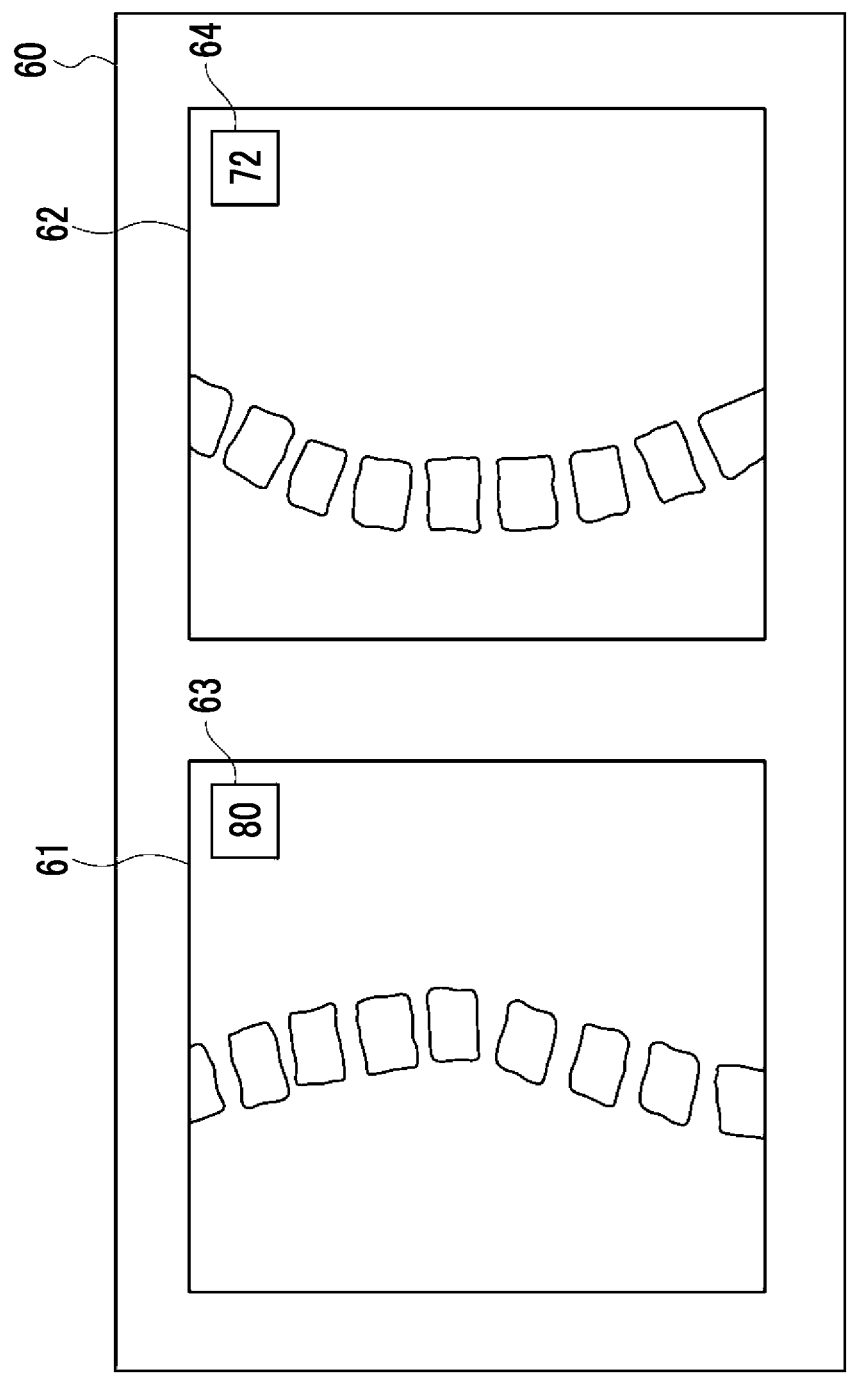
FIG. 19 is a diagram illustrating a display screen in a case in which a fracture risk is used as the evaluation result.

FIG. 19 is a diagram illustrating a display screen in a case in which the fracture risk is used as the evaluation result. As illustrated in FIG. 19, an evaluation result image 61 which is an enlarged image of a portion of the first bone portion image Gb1 and an evaluation result image 62 which is an enlarged image of a portion of the second bone portion image Gb2 including a vertebra corresponding to the evaluation result image 61 are displayed on a display screen 60. In addition, a fracture risk 63 as the first evaluation result R1 is displayed as a numerical value in the evaluation result image 61. A fracture risk 64 as the second evaluation result R2 is displayed as a numerical value in the evaluation result image 62. Further, the fracture risk illustrated in FIG. 19 becomes higher as the numerical value becomes larger. As such, the derivation and display of the fracture risks as the first and second evaluation results R1 and R2 make it possible to instruct patients at high risk of fractures to take preventive measures for fractures.

In addition, the bone mineral content derived for each small region may be mapped to the evaluation result images 61 and 62 illustrated in FIG. 19 as illustrated in FIG. 11, or the representative value of the bone mineral content derived for each small region may be given to the evaluation result images 61 and 62 as in FIG. 15. Further, as in FIG. 16, the bone mineral content may be mapped only to the cancellous bone region.

Further, in the above-described embodiment, the first and second radiographic images G1 and G2 and the third and fourth radiographic images G3 and G4 are acquired by the one-shot method. However, the first and second radiographic images G1 and G2 and the third and fourth radiographic images G3 and G4 may be acquired by a so-called two-shot method that performs imaging twice. In this case, the imaging conditions at the time of the acquisition of the first to fourth radiographic images G1 to G4 may be used as the imaging conditions for deriving the body thickness distribution and the scattered ray component. Further, in the case of the two-shot method, the position of the subject H included in the first and second radiographic images G1 and G2 and the third and fourth radiographic images G3 and G4 is likely to be shifted by the body movement of the subject H. Therefore, it is preferable to perform the process according to this embodiment after aligning the position of the subject in the first and second radiographic images G1 and G2 and the third and fourth radiographic images G3 and G4. For example, the method disclosed in JP2011-255060A can be used as the positioning process. For example, for first and second radiographic images G1 and G2, the method disclosed in JP2011-255060A generates a plurality of first band images and a plurality of second band images indicating structures having different frequency bands for each of first and second radiographic images G1 and G2, acquires the amount of positional deviation between the corresponding positions in the first band image and the second band image of the corresponding frequency band, and aligns the first radiographic image G1 and the second radiographic image G2 on the basis of the amount of positional deviation.

Further, in the above-described embodiment, the bone portion image derivation unit 23 derives the first bone portion image Gb1 from the first and second radiographic images G1 and G2. However, the present disclosure is not limited thereto. The first radiographic image G1 or the second radiographic image G2 may be used as the first bone portion image Gb1.

Further, in the above-described embodiment, the bone portion image derivation unit 23 derives the second bone portion image Gb2 from the third and fourth radiographic images G3 and G4. However, the present disclosure is not limited thereto. The third radiographic image G3 or the fourth radiographic image G4 may be used as the second bone portion image Gb2.

Further, in the above-described embodiment, two radiation detectors 5 and 6 are used to acquire two radiographic images for each of the front and side of the subject H, and the first and second bone portion images Gb1 and Gb2 are derived from the two radiographic images. However, the present disclosure is not limited thereto. Only one radiation detector may be used to acquire one radiographic image for each of the front and side of the subject H. In this case, the radiographic images for the front and side of the subject H may be used as the first bone portion image Gb1 and the second bone portion image Gb2, respectively.

Further, in the above-described embodiment, the subject H is irradiated with X-rays from the front and side to capture the images of the subject H. However, the subject H may be irradiated with X-rays from the back and side to capture the images of the subject H. Furthermore, the first direction and the second direction in which the subject H is irradiated with X-rays are not limited to the front (back) and side of the subject H. The first and second directions may be any directions as long as the images of a target bone portion included in the subject H are captured in different directions. In addition, the angle formed between the first direction and the second direction is preferably equal to or greater than 60 degrees and equal to or less than 120 degrees, more preferably equal to or greater than 80 degrees and equal to or less than 100 degrees, and most preferably 90 degrees at which the subject H is irradiated with X-rays from the front (back) and side.

Further, in the above-described embodiment, the comparison between the bone mineral contents of each small region over time may be performed using the first bone portion image Gb1 and the second bone portion image Gb2 derived by capturing the images of the same subject H at different imaging dates and times. FIG. 20 is a diagram illustrating the comparison between the bone mineral contents over time. In addition, FIG. 20 illustrates only the same vertebra included in two first bone portion images Gb11 and Gb12 which are front images captured at different imaging dates and times for the sake of explanation. As illustrated in FIG. 20, the same vertebra is compared between the first bone portion images Gb11 and Gb12 to check a change in the bone mineral content for each small region of the same vertebra. That is, in a case in which a medicine is administered, it is possible to check the effectiveness of the medicine in each small region. In addition, in a case in which only the progress is observed, it is possible to check a change in bone mineral content, that is, the progression of osteoporosis in each small region.

Figure 21:
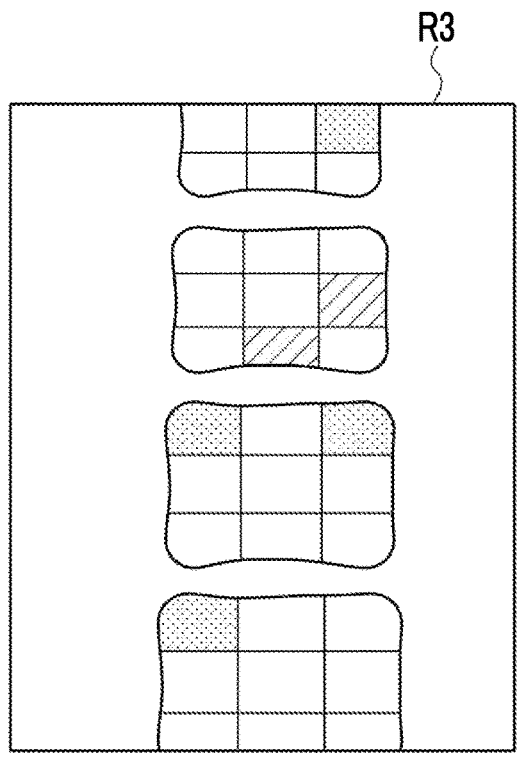
FIG. 21 is a diagram illustrating a change in the bone mineral content over time.

Further, as illustrated in FIG. 21, a difference in bone mineral content may be derived between the corresponding regions, and a difference value may be mapped to the bone portion image to derive the evaluation result. In addition, in an evaluation result R3 illustrated in FIG. 21, a small region for which the bone mineral content has increased is hatched in a diagonal direction, and a small region for which the bone mineral content has decreased is hatched in a dot shape. Further, a small region for which the bone mineral content has not changed is not hatched. This makes it possible to more easily check an increase or decrease in the bone mineral content for each small region.

Figure 22:
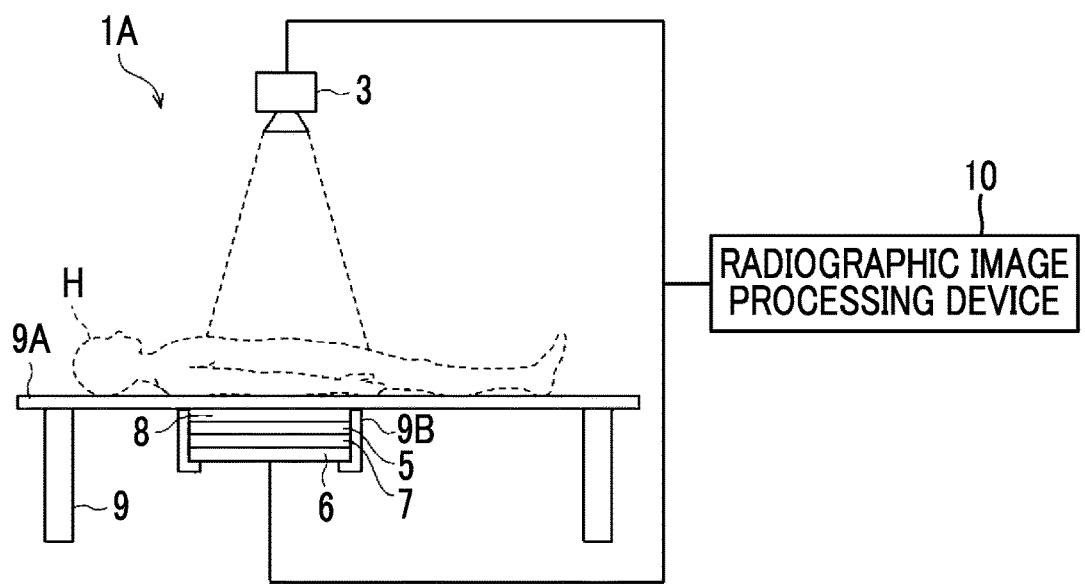
FIG. 22 is a block diagram schematically illustrating a configuration of a radiography system to which a radiographic image processing device according to another embodiment of the present disclosure is applied.

Furthermore, in the above-described embodiment, the image of the subject H in an upright position is captured. However, as illustrated in FIG. 22, the image of the subject H in a decubitus position may be captured. An imaging apparatus 1A in a radiography system illustrated in FIG. 22 is an imaging apparatus for acquiring a radiographic image of the subject H who lies on an imaging table 9 in a supine position or a lateral decubitus position. In addition, FIG. 22 illustrates a state in which the subject H is lying in the supine position. In the imaging apparatus 1A illustrated in FIG. 22, the first radiation detector 5, the X-ray energy conversion filter 7, and the second radiation detector 6 are arranged in this order from the side closer to the X-ray source 3. Further, a scattered ray removal grid 8 (hereinafter, simply referred to as a grid) for removing the scattered ray component scattered by the subject H in the radiation transmitted through the subject H is disposed between a top plate 9A of the imaging table 9 and the first radiation detector 5. The grid 8, the first radiation detector 5, the X-ray energy conversion filter 7, and the second radiation detector 6 are detachably attached to the imaging table 9 by an attachment portion 9B that is provided on a lower surface of the top plate 9A of the imaging table 9.

In a case in which the imaging apparatus 1A illustrated in FIG. 22 is used, the top plate 9A of the imaging table 9 and the grid 8 are interposed between the subject H and the first radiation detector 5. In addition, in the imaging apparatus 1 illustrated in FIG. 1 and the imaging apparatus 1A illustrated in FIG. 22, in some cases, air is interposed between the subject H and the first radiation detector 5 at the time of imaging. In this case, the first radiation detector 5 is irradiated with the radiation transmitted through the subject H through the top plate 9A, the grid 8, and an air layer. Here, objects, such as the top plate 9A, the grid 8, and air, have unique radiation characteristics. Therefore, since the radiation is transmitted through the objects, the quality of the primary ray component and the scattered ray component transmitted through the subject H changes depending on the radiation characteristics of the objects. For this reason, in this embodiment, it is preferable to consider the radiation characteristics of the objects interposed between the subject H and the first radiation detector 5 in a case in which the estimation of the body thickness distribution using the first radiographic image G1 and the removal of the scattered ray component are performed.

Specifically, the primary ray transmittance and the scattered ray transmittance of radiation corresponding to the types of objects interposed between the subject H and the first radiation detector 5 are generated as, for example, a table in advance according to various imaging conditions and the body thickness distribution of the subject H and are stored in the storage 13. Then, in a case in which the body thickness derivation unit 22 estimates the body thickness distribution of the subject H, it acquires the radiation characteristics of the objects corresponding to the body thickness distribution, that is, the primary ray transmittance and the scattered ray transmittance of the radiation with reference to the table. In addition, the body thickness derivation unit 22 acquires an estimated primary ray image and an estimated scattered ray image, using the acquired radiation characteristics, imaging conditions, and body thickness distribution, and combines the estimated primary ray image and the estimated scattered ray image to generate an estimated image. Further, the generation of the estimated image and the correction of the body thickness distribution are repeated until the difference between the estimated image and the first radiographic image G1 satisfies a predetermined end condition. Therefore, the body thickness derivation unit 22 derives the body thickness distribution in a case in which the end condition is satisfied as the body thickness distribution T1(x, y) of the subject H. Further, the bone portion image derivation unit 23 subtracts the estimated scattered ray image in a case in which the body thickness distribution satisfying the end condition is acquired from the first radiographic image G1 to remove the scattered ray components from the first radiographic image G1 in consideration of the radiation characteristics of the objects interposed between the subject H and the first radiation detector. In addition, similarly, the scattered ray components can be removed from the second radiographic image G2, the third radiographic image G3, and the fourth radiographic image G4.

In addition, in the above-described embodiment, the radiation is not particularly limited. For example, α-rays or γ-rays other than X-rays can be applied.

In the above-described embodiment, for example, the following various processors can be used as a hardware structure of processing units performing various processes, such as the image acquisition unit 21, the body thickness derivation unit 22, the bone portion image derivation unit 23, the first derivation unit 24, the second derivation unit 25, and the display control unit 26. The various processors include, for example, a CPU which is a general-purpose processor executing software (program) to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. A radiographic image processing device comprising:
   at least one processor,
   wherein the processor is configured to:
   acquire at least one first-direction radiographic image on the basis of first imaging that irradiates a subject including a bone portion with radiation in a first direction and acquire at least one second-direction radiographic image on the basis of second imaging that irradiates the subject with the radiation in a second direction different from the first direction;
   derive a bone mineral content for each pixel in the bone portion included in each of the first-direction radiographic image and the second-direction radiographic image; and
   divide the bone portion included in the first-direction radiographic image into a plurality of small regions, derive a first evaluation result for the bone portion in each small region on the basis of the bone mineral content derived for the first-direction radiographic image, divide the bone portion included in the second-direction radiographic image into a plurality of small regions, and derive a second evaluation result for the bone portion in each small region on the basis of the bone mineral content derived for the second-direction radiographic image.

2. The radiographic image processing device according to claim 1,
   wherein the first direction is a direction in which a front or back of the subject is irradiated with the radiation, and
   the second direction is a direction in which a side of the subject is irradiated with the radiation.

3. The radiographic image processing device according to claim 1,
   wherein the processor is configured to:
   derive a maximum value of a first body thickness of the subject in the first direction on the basis of the second-direction radiographic image and derive a maximum value of a second body thickness of the subject in the second direction on the basis of the first-direction radiographic image; and
   derive the bone mineral content, from which an influence of a scattered ray component of the radiation included in the first-direction radiographic image and the second-direction radiographic image has been removed, on the basis of the maximum value of the first body thickness and the maximum value of the second body thickness.

4. The radiographic image processing device according to claim 3,
   wherein the processor is configured to derive the bone mineral content, from which the influence of the scattered ray component of the radiation has been removed, on the basis of radiation characteristics of an object interposed between a radiation source that emits the radiation and radiation detectors that acquire the first-direction radiographic image and the second-direction radiographic image.

5. The radiographic image processing device according to claim 1,
   wherein the processor is configured to:
   perform, as the first imaging, imaging that irradiates the subject with radiation having different energy distributions in the first direction to acquire a first radiographic image and a second radiographic image as the first-direction radiographic images;
   derive a first bone portion image, in which the bone portion of the subject has been highlighted, on the basis of the first radiographic image and the second radiographic image; and
   derive the bone mineral content for each pixel of the first-direction radiographic image on the basis of the first bone portion image.

6. The radiographic image processing device according to claim 1,
   wherein the processor is configured to:
   perform, as the second imaging, imaging that irradiates the subject with radiation having different energy distributions in the second direction to acquire a third radiographic image and a fourth radiographic image as the second-direction radiographic images;
   derive a second bone portion image, in which the bone portion of the subject has been highlighted, on the basis of the third radiographic image and the fourth radiographic image; and
   derive the bone mineral content for each pixel of the second-direction radiographic image on the basis of the second bone portion image.

7. The radiographic image processing device according to claim 1,
   wherein, in a case in which the bone portion is a vertebral body included in a vertebra, the small regions are regions obtained by dividing the vertebral body in at least one of an up-down direction or a left-right direction in the first-direction radiographic image and the second-direction radiographic image.

8. The radiographic image processing device according to claim 1,
   wherein the processor is configured to derive the first evaluation result and the second evaluation result on the basis of an alignment of a spine in a case in which the bone portion is a vertebral body included in a vertebra.

9. The radiographic image processing device according to claim 1,
   wherein the processor is configured to derive the first evaluation result and the second evaluation result only for a cancellous bone region in a case in which the bone portion is a vertebral body included in a vertebra.

10. The radiographic image processing device according to claim 1,
    wherein the processor is configured to display the first evaluation result and the second evaluation result on a display.

11. The radiographic image processing device according to claim 10,
    wherein the processor is configured to display the first evaluation result and the second evaluation result so as to be superimposed on a three-dimensional image of the bone portion.

12. The radiographic image processing device according to claim 1, wherein the processor is configured to:
acquire a plurality of first-direction radiographic images and a plurality of second-direction radiographic images captured at different imaging times;
derive the bone mineral content for each imaging time; and
derive the first evaluation result and the second evaluation result on the basis of a change in the bone mineral content of each of the small regions of the plurality of first-direction radiographic images and the plurality of second-direction radiographic images over time.

13. The radiographic image processing device according to claim 12,
wherein the first evaluation result and the second evaluation result are an effectiveness of a medicine on the bone portion.

14. A radiographic image processing method comprising:
acquiring at least one first-direction radiographic image on the basis of first imaging that irradiates a subject including a bone portion with radiation in a first direction and acquiring at least one second-direction radiographic image on the basis of second imaging that irradiates the subject with the radiation in a second direction different from the first direction;
deriving a bone mineral content for each pixel in the bone portion included in each of the first-direction radiographic image and the second-direction radiographic image; and
dividing the bone portion included in the first-direction radiographic image into a plurality of small regions, deriving a first evaluation result for the bone portion in each small region on the basis of the bone mineral content derived for the first-direction radiographic image, dividing the bone portion included in the second-direction radiographic image into a plurality of small regions, and deriving a second evaluation result for the bone portion in each small region on the basis of the bone mineral content derived for the second-direction radiographic image.

15. A non-transitory computer-readable storage medium that stores a radiographic image processing program that causes a computer to perform:
a procedure of acquiring at least one first-direction radiographic image on the basis of first imaging that irradiates a subject including a bone portion with radiation in a first direction and acquiring at least one second-direction radiographic image on the basis of second imaging that irradiates the subject with the radiation in a second direction different from the first direction;
a procedure of deriving a bone mineral content for each pixel in the bone portion included in each of the first-direction radiographic image and the second-direction radiographic image; and
a procedure of dividing the bone portion included in the first-direction radiographic image into a plurality of small regions, deriving a first evaluation result for the bone portion in each small region on the basis of the bone mineral content derived for the first-direction radiographic image, dividing the bone portion included in the second-direction radiographic image into a plurality of small regions, and deriving a second evaluation result for the bone portion in each small region on the basis of the bone mineral content derived for the second-direction radiographic image.

* * * * *